United States Patent
Gratzl et al.

(10) Patent No.: US 6,859,767 B2
(45) Date of Patent: Feb. 22, 2005

(54) SHAPE OPTIMIZATION TO SOLVE INVERSE PROBLEMS AND CURVE/MODEL FITTING PROBLEMS

(75) Inventors: Miklos Gratzl, Mayfield Heights, OH (US); Sumitha Nair, Cleveland Heights, OH (US)

(73) Assignee: Case Western Reserve University, Cleveland, OH (US)

( * ) Notice: Subject to any disclaimer, the term of this patent is extended or adjusted under 35 U.S.C. 154(b) by 0 days.

(21) Appl. No.: 10/681,611

(22) Filed: Oct. 8, 2003

(65) Prior Publication Data

US 2004/0102933 A1 May 27, 2004

Related U.S. Application Data

(60) Provisional application No. 60/416,993, filed on Oct. 8, 2002.

(51) Int. Cl.[7] .............................................. G06F 19/00
(52) U.S. Cl. .............................. 702/194; 703/11; 703/12
(58) Field of Search ................................ 702/194, 189, 702/196; 703/11, 12, 2

(56) References Cited

U.S. PATENT DOCUMENTS

2002/0091666 A1 * 7/2002 Rice et al. ...................... 707/1
2003/0018457 A1 * 1/2003 Lett et al. ..................... 703/11
2003/0032576 A1 * 2/2003 Schilling ........................ 514/1
2004/0033975 A1 * 2/2004 Fu et al. ........................ 514/44

OTHER PUBLICATIONS

Wittmann et al., "Mass Spectrometry for Metabolic Flux Analysis", 1999.*

* cited by examiner

*Primary Examiner*—Patrick Assouad
(74) *Attorney, Agent, or Firm*—Fay, Sharpe, Fagan, Minnich & McKee, LLP

(57) ABSTRACT

A method for solving deconvolution problems where it is desired to reconstruct a signal over a time range or another variable of interest involves comparing shapes of measured and reconstructed plots. The optimization method is based on minimizing the error in shape (as opposed to the square errors in amplitude). A shape approach method characterizes similarity of two functions by computing the angle between the two when they are treated as two vectors in the n dimensional space where n is the number of data points it is desired to consider from both functions (the functions themselves may consist of more than n data points). A new approximation is then created by trying to decrease the disimilarity between the actual and predicted functions. This dissimilarity is measured as the angle between the two corresponding vectors, so the measure of dissimilarity is the size of the angle. A much closer matching between the reconstructed plot and what may be expected in practice is achieved with this method than is conventionally achieved with least squares or Fourier transform methods.

24 Claims, 14 Drawing Sheets

SHAPE OPTIMIZATION TO SOLVE INVERSE PROBLEMS AND CURVE/MODEL FITTING PROBLEMS

This application claims the benefit of U.S. patent application Ser. No. 60/416,993, filed on Oct. 8, 2002, which is incorporated herein in its entirety, by reference.

BACKGROUND OF THE INVENTION

1. Field of the Invention

The invention relates to a method for solving deconvolution problems where it is desired to reconstruct a signal over a time range or another variable of interest. It finds particular application in determining a flux from a source which is spaced from a detector, such as determining flux from a biological cell or layer of cells, and will be described with particular reference thereto. It will be appreciated, however, that the invention is equally applicable to a wide range of deconvolution problems, curve fitting problems, spectral shape recognition and analysis, calibration, and the like, where the independent variable may be time or spatial or other coordinates.

2. Discussion of the Art

Transport at the cellular level is an essential element for sustaining life. Anomalies in cellular transport have been associated with a host of conditions, ranging from Cystic Fibrosis to Multidrug Resistance (MDR) in cancer cells. In order to treat such life threatening conditions, it is desirable to develop a qualitative and quantitative understanding of the underlying transport mechanisms and their anomalies. Cellular release is a very common mode of transport used by cells to make adjustments to changes in their environment in order to maintain homeostasis and to respond to external stimuli. Hence, understanding of the type and quantities of species released by a particular cell type can assist in understanding the associated biological processes taking place.

Transport at a cell cluster, or at single cells, may involve release, cellular efflux, uptake, mass transport in the extracellular medium, or any combination of these processes. The quantity characterizing these processes is generally called a flux, or a flux density, and is expressed in units of moles (or weight) per unit area per unit time. The ability to provide accurate plots of flux over time has particular application in the study of cellular transport mechanisms.

There are many applications when it is desirable to reconstruct flux values from signals detected some distance from the source of the flux. For example, in studying efflux of a chemical, such as an ion or drug, from a monolayer of biological cells, such as human or other animal cells, the monolayer is covered by a liquid, such as a cell medium or buffer. A sensor, such as an electrode system, is placed in contact with the liquid, at a finite distance from the monolayer. The sensor measures a concentration of the drug or ion (hereinafter chemical species) in the adjacent liquid, rather than the actual flux of the drug or ion secreted from the monolayer. This is because the measured concentration depends on not only the efflux at the monolayer surface, but also on the diffusion of the chemical species, and the distance of the sensor from the monolayer. The chemical species passes into the liquid and diffuses through the liquid toward the sensor over time, at a rate governed by the diffusion constant. While concentration measurements can provide some useful information, they can give only an indirect indication of the flux at the cells. This is because the flux across the plasma membrane in either direction induces a secondary form of transport in the extracellular medium or space, whose own, relatively slow dynamics can largely affect what the sensor actually senses. It is therefore desirable to reproduce, as closely as possible, the flux values at the cells, which provide a more accurate picture of what is going on at the cell level.

Current measurement schemes for directly obtaining flux values at a cell's or cell cluster's surface are limited to the study of some charged particles (a few inorganic ions) and are restricted in the information they provide due to the lack of sufficient sensitivity. Hence, in most contexts, flux values have to be indirectly reconstructed from concentration changes monitored at some fixed distance from the cell site.

For determination of ionic fluxes, the concentration is generally measured by placing an ion selective electrode at a fixed distance from the surface of the cell monolayer. The ion selective electrode produces a voltage change corresponding to the change in the concentration of the specific ion that it is designed to measure. For example, a potassium ion selective electrode shows a potential change corresponding to a change in concentration of potassium ions. Irrespective of the measurement scheme used, the concentration that is measured is not a direct indication of the secretion flux. This is because the concentration is affected by other parameters, such as the distance of sensor from the monolayer, the diffusivity of the ions in the solution, and the dynamics of mass transport between the source and the sensor.

To derive flux from measured concentrations, the mass transport from cells to the sensor is computationally "undone". This leads to deconvolution, which is known to be a problematic mathematical operation.

Mathematical expressions for the relationships between concentration and flux have been developed. By assuming mass transport to be planar and one dimensional, the measured concentration can be related to the secretion flux by the differential equation:

$$\frac{\partial C}{\partial t} = D \frac{\partial^2 C}{\partial z^2} \qquad (1)$$

where t is the time (seconds);

z is the distance from the monolayer (cm);

F is the flux at the cell monolayer (e.g., in (mmol cm$^{-2}$ s$^{-1}$), which can be expressed as a function of time: F(t) represents the flux at the surface at a time corresponding to the time at the which the emitted flux was generated;

C is the measured concentration (e.g., in mmol cm$^{-3}$), which can be expressed as a function of distance from the monolayer and time: C(z,t); and D is the diffusion constant.

C(z,0)=0 is the initial condition. i.e., at time t=0 the concentration at a distance z from the monolayer is zero. Other initial conditions may exist, however.

The assumption of planar mass transport is generally valid where sufficient time has passed before any measurement such that the diffusion zones of the different point sources (cells within the monolayer) fully overlap. The electrode is placed far enough from the monolayer of cells so that it "sees" the sources as one planar source. There is no diffusion in the negative z direction and hence the assumption of one dimensional diffusion is also valid.

The boundary condition is represented by the expression:

$$F(t) = -\frac{D}{A}\left(\frac{\partial C}{\partial z}\right)_{z=0} \quad (2)$$

where F is as defined above and A is the surface area of the monolayer.

The diffusion problem can be expressed by the equation:

$$\delta_{z,t} = \frac{1}{\sqrt{\pi D t}} \exp\left(\frac{-z^2}{4Dt}\right) \quad (3)$$

The delta function in this equation translates the effect of secretion at a cell surface, $(-F(t))$ (mmol cm$^{-2}$ s$^{-1}$) into an amount of material in a unit volume, $C_z(t)$ (mmol cm-3) over a period of time and hence has a unit of cm$^{-1}$. The general solution to the diffusion expression is provided by the expression:

$$C_z(t) = \int_0^t F(t')\delta(t-t')dt' \quad (4)$$

where F (t') represents the flux at the surface at a time t', corresponding to the time at which the emitted flux corresponding to the measured concentration was generated.

The measured concentration C(t) is a convolution of the flux F(t) with the delta function (Eqn. 4). Hence the convolution of flux with the delta function is often described as a "forward problem," the solution of which is the measured concentration. Deriving the flux from the measured concentration is called the "inverse problem." Various methods have been used to solve this "inverse" problem (obtaining F(t) knowing C(t)), often termed "deconvolution". In general, a plot of measured concentrations over time is compared with a plot of concentrations obtained from a proposed flux over time. The currently available methods, however, do not usually achieve a close fit with the actual flux plot.

Inverse Fourier Transform and Error Minimization techniques are the most commonly used tools for solving such deconvolution problems. In the Inverse Fourier Transform method, Fourier transform techniques are used to generate the flux plots. The Fourier transform utilizes the following expression in its calculations:

$$F(t)=F^{-1}[F(C_z(t))]/F[\delta(t)]) \quad (5)$$

where F denotes the Fourier operation and F$^{-1}$ denotes its inverse.

Fourier transform methods have been widely used for a number of deconvolution applications, in part because the complicated integration in the time domain is converted into simple multiplication in the Fourier domain. However the Fourier transform theory makes assumptions which are not valid in all applications. For example, the method assumes that the function (flux in the present case) to be determined is a periodic one. In many instances, such as the flux from cells, this assumption is invalid. Moreover, it assumes that negative flux values are possible, which again does not generally correspond with reality. Moreover, for cell mass transport, the resulting flux is not an instantaneous result of whatever is its cause, but rather occurs after a time delay. This again contributes to errors in the reconstructed flux data, such as negative values for the reconstructed flux.

Thus, due to artifacts introduced to the deconvolution based on these and other assumptions, the proposed flux does not accurately correspond with the actual flux. This tends to get even worse after repeating the procedure several times. The resulting plots often have negative flux values or sudden and unrealistic drops or increases in flux. More importantly, the computed flux will not reproduce the measured concentration plot when inserted into the forward problem.

In another method, error minimization, based on a least squares errors (LSQ) technique, is used to solve the inverse problem. In the LSQ method, error is defined as $$C_r(t)=[C_r(t_1)C_r(t_2) \ldots ];$$
$$C_s(t)=[C_s(t_1)C_s(t_2) \ldots ] \quad (6)$$
$$\text{Error}=\sqrt{(C_r(t_1)-C_s(t_1))^2+(C_r(t_2)-C_s(t_2))^2+\ldots}$$

Where subscripts r and s correspond to real (actual) and assumed starting concentrations, respectively.

Error minimization techniques are aimed at optimizing square errors. Error minimization is performed using $\min_{F(t)}$ [error $(C_r(t), C_s(t))$], where $C_r(t)$=real or actual concentration (mmol cm$^{-3}$);

$F_s(t)$=starting flux (mmol cm$^{-2}$s$^{-1}$) and $C_s(t)$=concentration corresponding to the starting flux (mmol cm$^{-3}$)

$C_r(t)$ is the concentration that is measured and hence is referred to as the measured or actual concentration, even though artifacts in the measuring device may lead to less than actual values being generated. To apply the least squares technique, a flux $F_s(t)$ is assumed and the concentration $C_s(t)$ corresponding to this flux is calculated using Equation 4. The error between $C_s(t)$ and $C_r(t)$ is calculated using Equation 6. The Flux value is then changed so that the error between $C_s(t)$ and $C_r(t)$ is decreased. The solution goes through numerous iterations, with the expectation that each time, the proposed flux plot will more closely correspond with the actual flux plot. This is tested by the difference between the actual concentration plot and the one predicted from the flux.

The method uses directional stepping in which each element of a flux vector is stepped, keeping the others constant. Based on these operations, a new flux vector is determined. The concentration corresponding to this new flux vector is then calculated. The error between the real concentration and the concentration obtained by stepping the elements of the flux vector is then calculated. This gives a directional error vector, which is the partial derivative of error with respect to individual elements of the flux vector.

This technique tends to introduce noise, unrealistic shapes in the flux and concentration plots, and instability into the results.

The present invention provides a new and improved optimization method which overcomes the above-referenced problems and others.

SUMMARY OF THE INVENTION

In accordance with one aspect of the present invention, a method for determining an approximation of a first function from a second function is provided. There is a forward solution for calculating the second function from the first function. The first function describes the relationship of a first variable to an independent variable. The second function describes the relationship of a second variable to the independent variable, the second variable being one that is ascertainable. The method includes providing the second function, applying a shape approach method to produce the approximation of the first function. This step includes comparing a shape of the second function with a shape of a reconstructed second function derived from a proposed first function, the proposed first function describing a proposed relationship of the first variable to the independent variable. The method optionally further includes repeating steps of applying a shape approach method to produce the approximation of the first function a finite number of times.

In accordance with another aspect of the present invention, a method for determining an approximation of a flux of a species from a source over time from concentration of the species measured a distance from the source over time is provided. The method includes providing a function of the measured concentration over time, proposing a function of the flux over time, and applying a forward solution which relates the flux to the concentration to generate a reconstructed function of the concentration over time. The method further includes comparing the reconstructed function of the concentration with the function of the measured concentration. This step includes, for a plurality of data sets taken from the reconstructed function of the concentration over time, generating a first vector representing, the change in the reconstructed concentration between times $t_1$ and $t_2$, where $t_2$ is spaced from $t_1$. For a plurality of data sets taken from the function of the concentration over time, a second vector representing the change in the concentration between times $t_1$ and $t_2$ is generated. An angle between the first and second vectors for the set of data is determined. The proposed function of the flux over time is modified to provide a second proposed function of flux over time, such that when steps of generating a first vector and determining an angle are repeated the angle is decreased in value. Optionally, these steps and the modifying step are repeated a finite number of times to derive the approximation of the flux.

An advantage of at least one embodiment of the present invention is that a flux from a cell monolayer can be accurately calculated from concentration measurements taken some distance from the monolayer.

Another advantage of at least one embodiment of the present invention is that the efficacy of drugs on biological tissues can be determined.

Another advantage of at least one embodiment of the present invention is that it enables solutions to curve fitting problems, spectral shape recognition and analysis, calibration, and the like, where the independent variable may be time or spatial or other coordinates.

Still further advantages of the present invention will be readily apparent to those skilled in the art, upon a reading of the following disclosure and a review of the accompanying drawings.

DETAILED DESCRIPTION OF THE PREFERRED EMBODIMENT

A method for solving deconvolution problems where it is desired to reconstruct a signal over a time range or another variable of interest involves comparing shapes of measured and reconstructed plots. The optimization method is based on minimizing the error in shape (as opposed to the square errors in amplitude.

To characterize the similarity of two functions, the angle between the two functions is computed when they are treated as two vectors in the n dimensional space where n is the number of data points desired to be considered from both functions (the functions themselves may consist of more than n data points). In this way, an approximation of a function which is related to one of the two functions by a known relationship can be created by trying to decrease the disimilarity (or increase the similarity) between the actual and predicted functions. This dissimilarity is measured as an angle between two corresponding vectors, so the measure of dissimilarity is this angle. The aim is to decrease this angle to obtain better similarity.

This approach is discussed in the context of a specific biological problem which deals with obtaining release rates or flux from a monolayer of non oriented or oriented cells. An epithelial cell is an example of an oriented cell. Such cells are polarized in nature, i.e. they have distinct apical and basal sides which are functionally and structurally distinct from each other, and hence function only if grown as a monolayer. An AUXB1 cancer cell is an example of a non oriented cell.

In reconstructing flux from a cell monolayer, the shape method described herein computes the error between real and predicted concentration plots as the difference in shape of the two plots. This is obtained from the angular difference between vectors corresponding to each of several of the concentration data sets. One such vector is perceived as being represented in an n-dimensional space where n is the number of measured concentration data points, and the components of this vector are the respective measured values.

Figure 1:
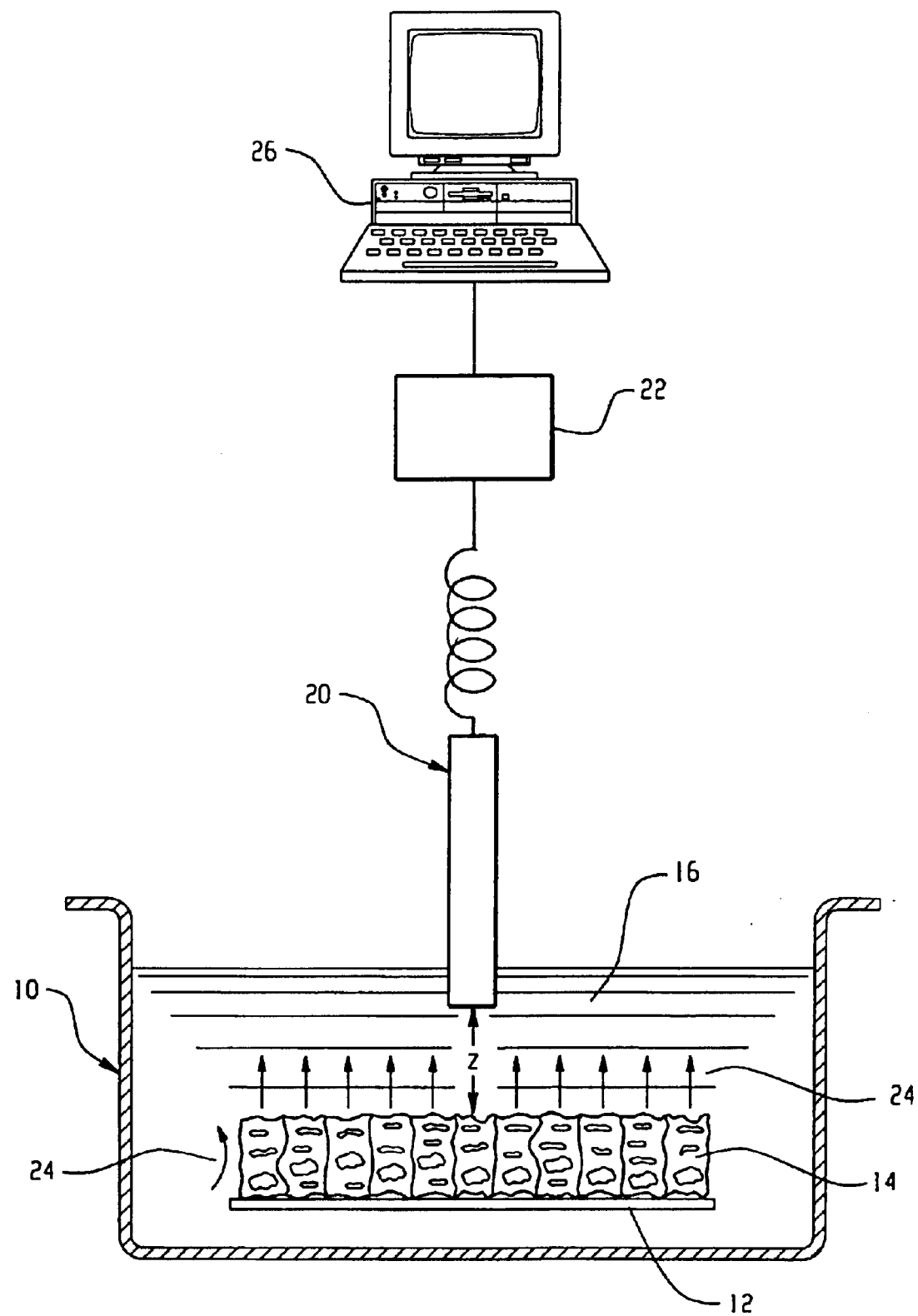
FIG. 1 is a schematic view of a system for detecting a concentration of a chemical species in a solution above a layer of cells.

With reference to FIG. 1, one embodiment of a system for detection of concentration of a chemical species (such as an ion or drug) is shown. The system includes a vessel 10, in which a substrate 12 carrying a cell 14 or population of cells is positioned. The cells are immersed in suitable liquid medium 16, e.g., an aqueous medium, such as a phosphate buffered saline covers the cell(s). Alternatively, the vessel may be eliminated, and a droplet of the medium is placed over the substrate on the cells. The cells may be in the form of an epithelium, grown as a monolayer, or be spatially arranged cells.

A sensor system 20 is positioned in fluid contact with the liquid, an average distance z from the cell membranes. The distance z can be precisely measured. The sensor system is electrically connected with suitable electrochemical monitoring and control equipment 22, such as a potentiostat or a high input impedance differential amplifier. In one embodiment, the cells have been treated with a drug, ion, or other chemical (chemical species), prior to placing the substrate in the liquid medium, and as a result, over time, the chemical species diffuses into the liquid medium and progresses to the sensor, where it is ultimately detected. In another embodiment, the cells are stimulated in the liquid medium with a secretagogue, such as a drug, and as a result, efflux of a chemical species occurs. A suitable processing system 26, such as a PC, receives signals from the sensor and converts the signals to concentration measurements.

Figure 2:
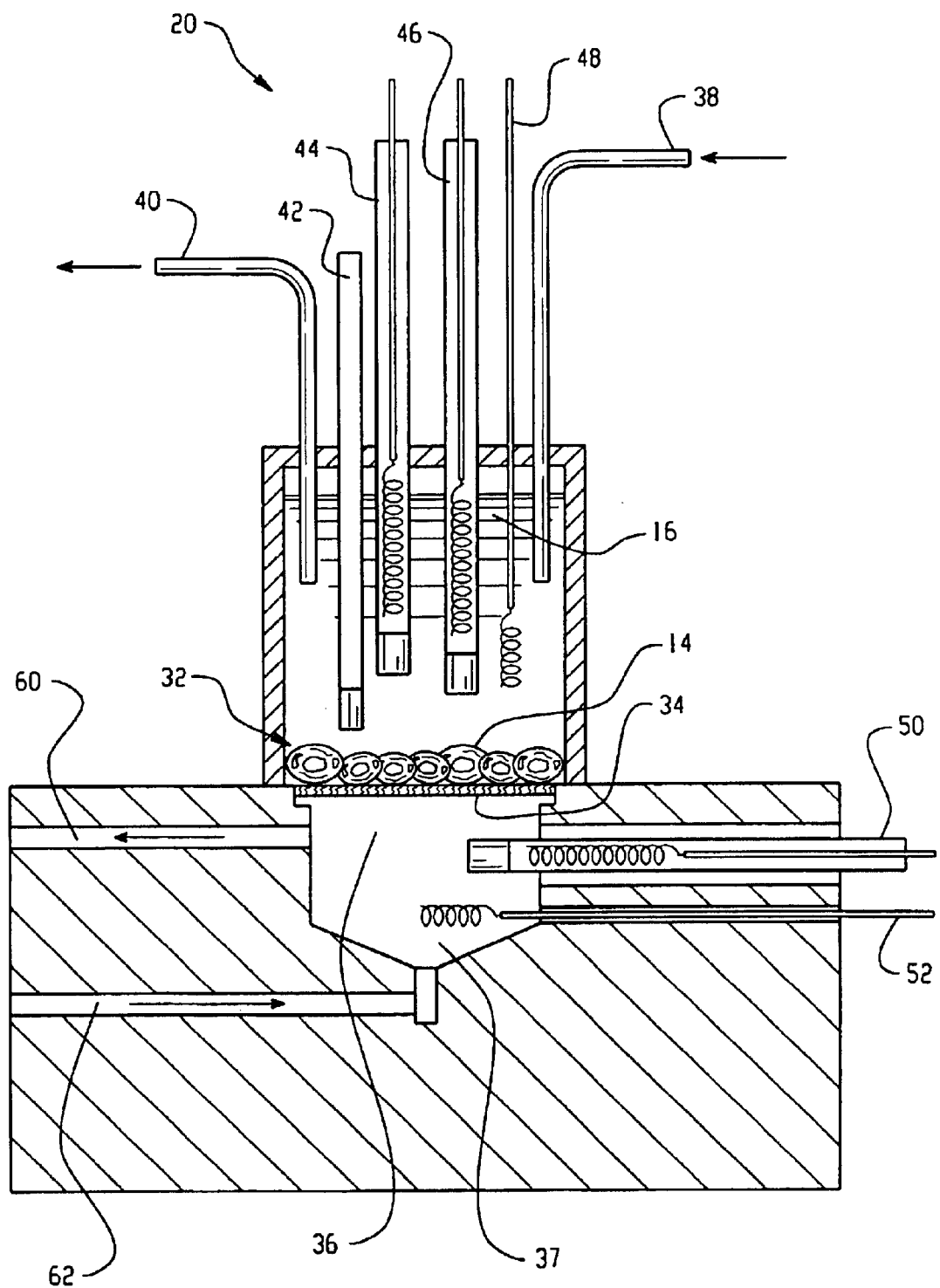
FIG. 2 is a side sectional view of one embodiment of the system of claim 1.

With reference to FIG. 2, an embodiment of the system for detection of concentration of a chemical species following apical stimulation with a secretagogue is shown. The system includes a vessel 30, such as an Ussing chamber, in which a monolayer 32 of cells 14, such as a confluent epithelial cell monolayer, is contained on a permeable substrate, such as a filter medium 34 in a first compartment 35 of the two compartment chamber 30. The cells can be grown on the permeable filter 34 so that they are in contact with a basal solution 36 on the basal side and an apical solution 16 on the apical side in an apical compartment 37 of the two-compartment chamber 30. The vessel includes an apical inlet 38 for introducing a chemical, such as a secretagogue, into the liquid medium 16 in the vessel and an apical outlet 40 for perfusion, to maintain the solution at a constant level. Where a monolayer of non oriented single cells is used, it will be appreciated that the cells can be simply seeded on a Petri dish.

The release of ions can be monitored with respective micro ion selective electrodes, at close distance, e.g., 10–100 micrometers ($\mu$m), to obtain data with good temporal resolution. The concentration is generally measured by placing an ion selective electrode at a fixed distance from the surface of the cell monolayer. The ion selective electrode produces a voltage change corresponding to the change in the concentration of the specific ion that it is designed to measure. For example, a potassium ion selective electrode shows a potential change corresponding to a change in concentration of potassium ions. The sensor system 20 may include a plurality of ion-selective microelectrodes for monitoring secretion of ions, such as $K^+$, $Na^+$, $H^+$, $Ca^{2+}$, and $Cl^-$ from the monolayer 32.

In the illustrated embodiment, electrodes 42, 44, 46, 48 50, 52 are provided. A first electrode 42 is an ion selective electrode, such as a chloride, sodium, hydrogen, or calcium ion selective electrode. Irrespective of the measurement scheme used the concentration that is measured is not a direct indication of the secretion flux. This is because the concentration is affected by other parameters like how far or close you place the sensor to the monolayer and the diffusivity of the ions in the solution. A reference ion selective electrode 44 and a conventional reference electrode 46, such as an Ag/AgCl electrode are also in contact with the apical solution 16. A conventional reference electrode 50 may also be positioned in the basal fluid 36. Electrodes 48 and 52 are current electrodes for injecting current across the monolayer. A basal outlet 60 and a basal inlet 62 are optionally provided for introducing a chemical, such as a secretagogue, into the liquid medium 36 in the basal chamber 37 and for perfusion and to maintain the solution at a constant level to the basal chamber, respectively.

Precise positioning of the ion selective electrode 42 can be achieved using electrochemical impedance in situ to monitor the distance z. As can be seen, the concentration plot differs quite considerably in shape from the actual flux, both in amplitude and in the time at which maximum concentration/flux is reached.

It will be appreciated that FIGS. 1 and 2 are exemplary only, and that any suitable arrangement for detecting concentration in a liquid medium at a distance from a cell or population of cells can be employed.

Using equipment such as that shown, concentration measurements are made over a period of time. The data is stored in the processor and a plot of concentration vs. time can be generated. The plot may have an appearance similar to the exemplary plot shown in FIG. 3. The object is to reconstruct the actual flux at the cell monolayer, represented by the exemplary plot in FIG. 4. As can be seen the concentration plot differs quite considerably in shape from the actual flux, both in amplitude and in the time at which maximum concentration is reached.

A novel shape optimization technique is used to reconstruct the flux plot. First, a first proposed flux plot is input into suitable processor. The processor applies the forward solution (Equation 4) to reconstruct a first reconstruction concentration plot for several, typically a large number, of data points on the plot. If this matches closely with the actual concentration plot, it can be assumed that the proposed flux plot accurately represents the actual flux. However, in the first iteration, the first reconstructed concentration plot will likely diverge significantly from the actual concentration plot. An algorithm is used which applies a vector analysis on a large number of data points on the actual concentration plot and on the equivalent data points for the first reconstruction plot. Using the vector analysis, the computer modifies the first proposed flux plot to create a second proposed flux plot and repeats the process.

The reconstruction process can undergo several iterations, each time more closely approximating the actual flux plot. Eventually, the processor determines that the actual and reconstructed concentration plots are congruent (or within statistically acceptable variations) and provides a plot of the last proposed flux plot which provides the closest match (the reconstructed flux). Alternatively, the processor may be programmed to repeat the process a selected number of times, such as twenty or fifty.

The accuracy of the reconstruction can be established using forward solution (Equation 4) to create a reconstructed concentration plot which is then superimposed over the actual concentration plot. An operator can readily confirm by viewing any differences between the two plots that the processor has represented the flux with reasonable accuracy.

The algorithm can be illustrated by using two elements for simplicity, by considering the concentration values at two times t1 and t2. Vectors are drawn representing the two data points of each curve. An angle $\theta$ between the two vectors for the actual and reconstructed concentration is indicative of a difference in shape between the two curves. Where $\theta$ is zero for a subset of the measured concentration curve, the two curves can be considered congruent for that particular time period. Such a representation shows how a function which comprises of N number of points/elements can be represented as a vector in the N dimensional space.

In an actual calculation, the value of $\theta$ is obtained for the entire set of data that are considered valid, i.e., using a large number of data points which correspond to a vector in a multidimensional space for the actual (or real) concentration plot, and another vector of the same dimensions for the reconstructed concentration plot, whose angle $\theta$ is a measure of the similarity in shape between the two curves. The two curves are perfectly similar in shape when this angle is zero.

In practice, it may not be desirable to continue the iterations till this condition is reached. One reason for this is that not only the major shape components but also all the random errors (noise) are perfectly reconstructed. Stopping the iterations before this happens thus serves as an efficient and tunable filtering performed at the same time as deconvolution is being performed. As a result, random errors are reduced.

The error in shape, i.e., the angle $\theta$, is computed in each iteration step and the flux vector is then changed such that this angle likely decreases in the next iteration step. One way of changing the flux vector is by computing the sensitivities of the angle $\theta$ with respect to each element of the vector, and then stepping each element in the direction of a negative predicted change in $\theta$. This is equivalent to moving the flux vector in the direction of the negative gradient of the angle $\theta$ as a function of the flux vector.

Figure 6:
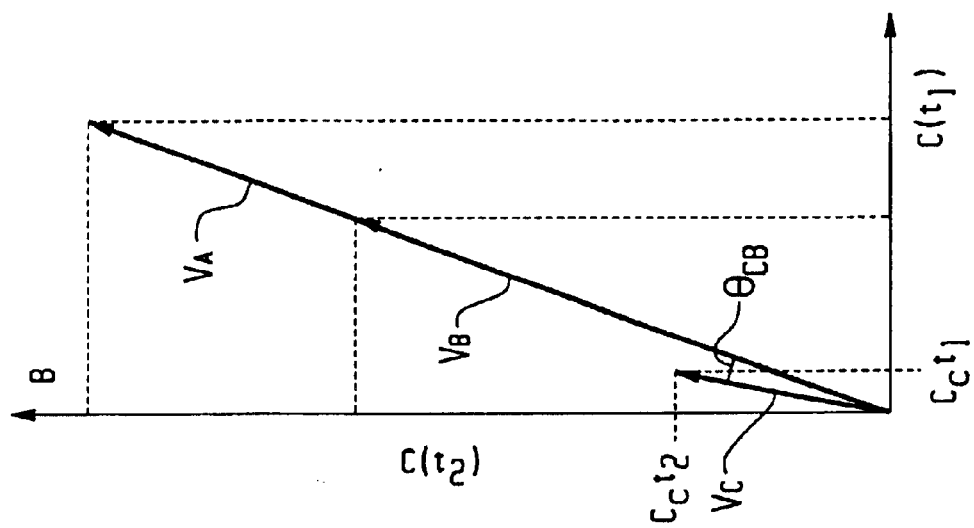
FIG. 6 is a vector diagram showing vectors for the three plots shown in FIG. 5.
Figure 5:
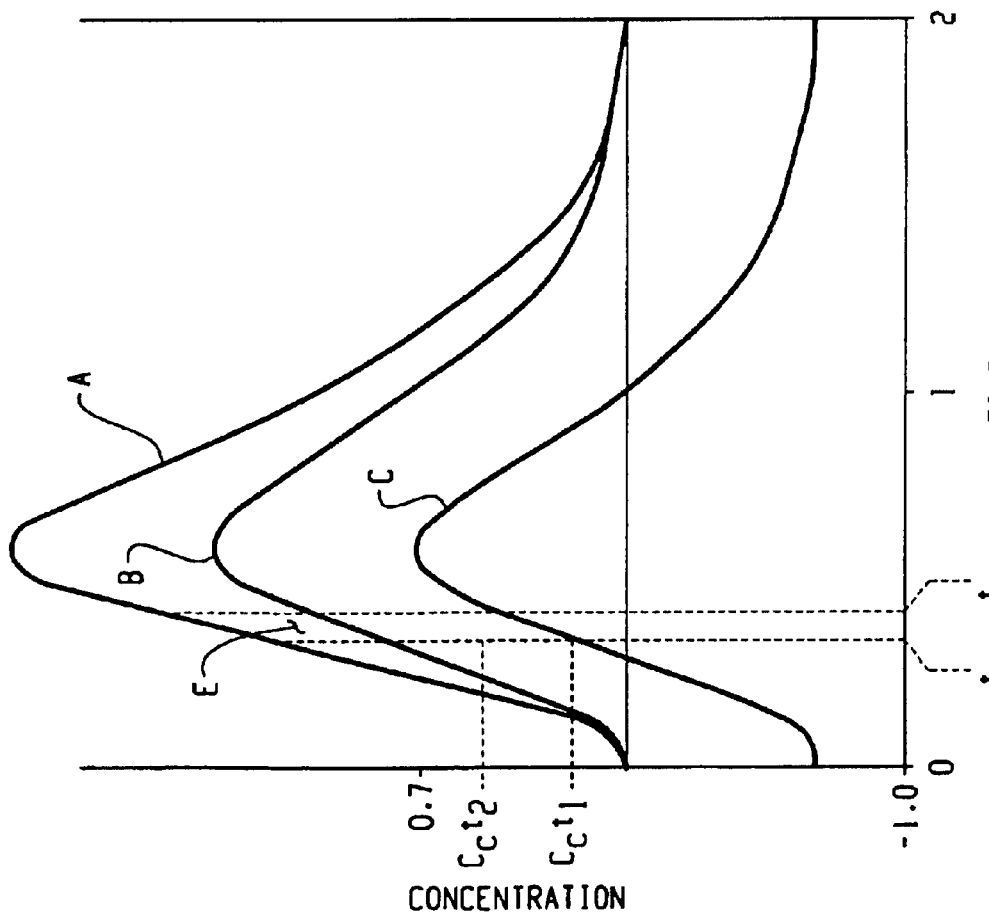
FIG. 5 is a plot showing three plots of concentration vs time.

For example, with reference to FIG. 5, three theoretical plots of concentration vs. time are shown, labeled A, B, and C. It will be appreciated that these do not represent actual concentration plots, but are merely intended to demonstrate the shape approach method. Vectors for each of these plots for the element E for time $t_1$–$t_2$ are shown in FIG. 6. The vectors are created as follows. The concentration $Ct_1$ at time $t_1$ is read off the graph and marked on the x axis($C(t_1)$). For example, in the case of plot C, concentration at time $t_1$ $C_C t_1$ is shown on both FIGS. 5 and 6. Then, the concentration at time $t_2$ $C_C t_2$ is plotted on the y axis ($C(t_2)$). A resultant vector $V_C$ is drawn between the origin and the point at which horizontal and vertical lines from the two values $C_C t_1$ and $C_C t_2$ meet. Vectors $V_A$ and $V_B$ for graphs A and B are created similarly. A pair of vectors can be compared to determine the value of $\theta$. In the case of vectors $V_C$ and $V_B$, $\theta_{CB}$ is a non-zero angle, indicating that the two plots B and C do not have the same shape. For example, if plot C represents a reconstructed plot of concentration and plot B represents an actual plot of concentration, then because $\theta_{CB}$ is a finite angle, it can be said that for the particular element E, that the two plots have a different shape. It can be seen that the reconstructed plot does not quite correspond with the actual plot.

In the case of plots A and B, the vectors $V_A$ and $V_B$ are congruent, and therefore $\theta$ (not illustrated for these vectors) is zero. For these vectors, it can be said that the shape is the same, even though the two plots A and B do not overlap in amplitude. Hence, the two plots can be similar or identical in shape irrespective of the amplitude involved. Similarity in shape is thus defined such that multiplication or division of every element of a plot by a constant will result in a perfectly similar plot.

The method provides a shape, rather than simply a set of amplitudes, as is the case in other reconstruction processes.

The angle $\theta$ indicates how close the two plots are for the particular data set E evaluated. Thus, the objective is to reduce $\theta$ to as close to zero as possible. When $\theta$ is zero the plots are congruent and further optimization of the data set is not needed. Where $\theta$ differs from zero, the algorithm adjusts the values in the next iteration of the reconstructed concentration plot.

Figure 3:
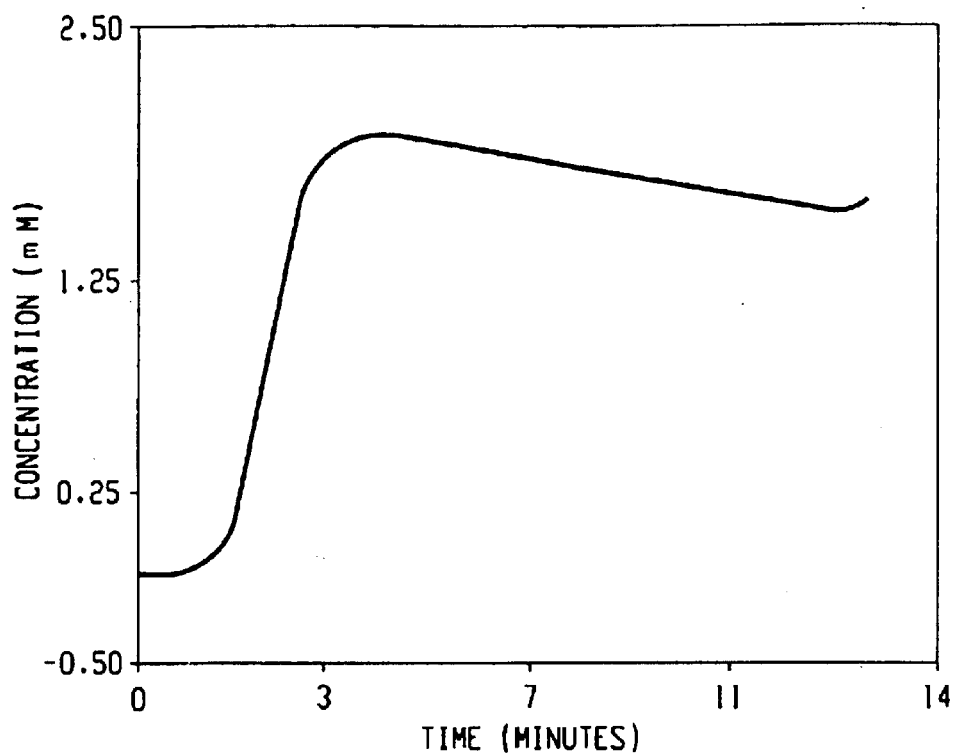
FIG. 3 is a representative plot of concentration of the chemical species vs time obtained with the system of FIG. 2.
Figure 4:
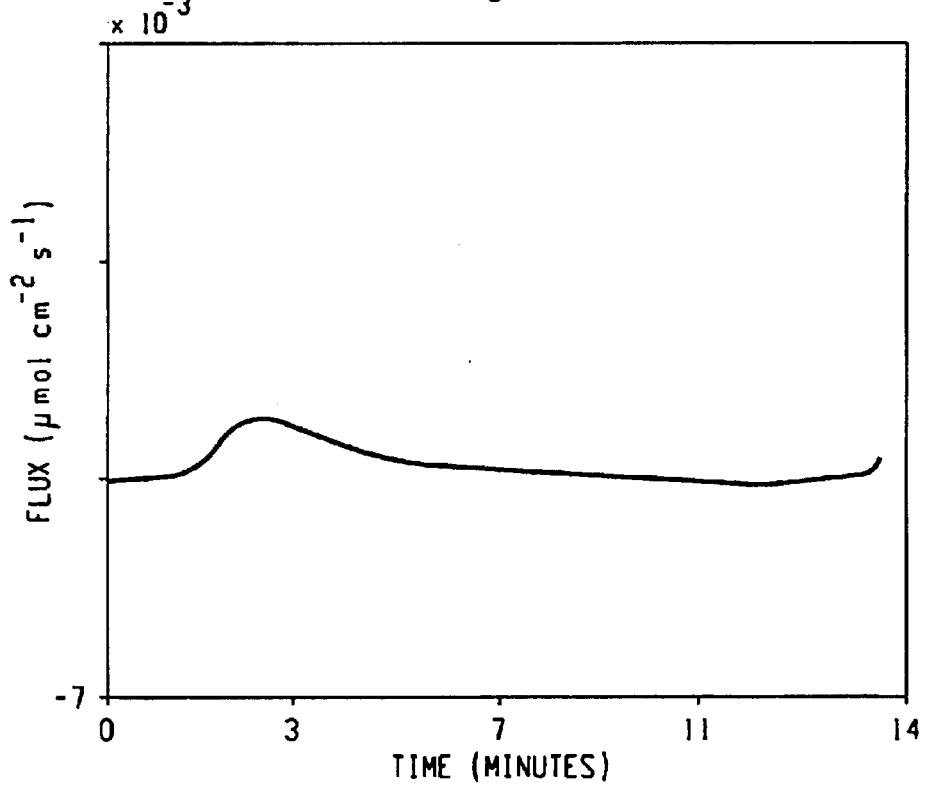
FIG. 4 is a representative plot of the corresponding flux vs. time which can be obtained by deconvolution of the plot of FIG. 4 with a shape approach.

For concentration plots similar to those shown in FIG. 3, the degree of convergence varies over time, giving different values of $\theta$ for each step of iteration. The algorithm attempts to optimize the reconstructed plot in the next iteration to bring the cumulative value of $\theta$ closer to zero.

To determine the actual value of $\theta$, one method is to calculate the dot product of the two vectors (representing the two plots to be compared) and then compute the inverse of the cosine of the dot product divided by the product of the absolute values of the two vectors:

$$\theta = \arccos\{\text{dot product of vector } \mathbf{1} \text{ and vector } \mathbf{2}/[\text{abs}(\text{vector } \mathbf{1}) \text{ times abs}(\text{vector } \mathbf{2})]\} \quad (7)$$

The value obtained (in degrees or radians) is a measure of difference in shape between the two plots, $\theta = 0$ being perfect similarity.

In one embodiment, the processing software attempts to minimize the errors in shape, i.e. $\theta$.

The shape optimization technique has application in a variety of contexts in addition to the study of drug efflux from cells. It enables a broad range of mathematical numerical operations to be performed more efficiently, providing more accurate results than with conventional computational techniques.

In one general application, the shape approach method can be used for determining a first function that is not directly measurable, from a second function that is measured, where there is a known method for calculating the second function from the first one. The first function can thus be a relationship between a first variable and an independent variable and the second function can be the relationship between a second variable and the independent variable, where the first variable has a relationship to the second variable. The first variable is one which is not directly measurable (such as flux, emitted amplitude, or the like). The independent variable can be time, wavelength, potential, or the like. The second variable can be a measured concentration, or the like. The first function may thus be a flux of molecules, energy, or light intensity versus time, or versus some other independent variable, such as spatial distance. The second function may be concentration of the same molecules versus time as induced by the flux that is to be determined, radiation pressure at some distance induced by energy flux, or tissue damage induced by light intensity at some distance.

One or more of the following steps may be used.
1. Applying the shape approach method to produce a close approximation of a first function Funct.1 corresponding to a plurality of values S1 of a first variable as a function of an independent variable (e.g., a plot of flux as a function of time), including:
    a) providing a second (measurable) function Funct.2 corresponding to a set of values S2 of a second variable as a function of the independent variable (these may be actual measured values or values taken from a plot of actual values, e.g., a plot of concentration over time);
    b) selecting a first proposed function Funct.1A comprising a set of values S1A of the first variable as a function of time. (This step may use a processor's stored knowledge of a typical plot of the first variable vs the independent variable, or be simply a preselected shape, such as a straight line, curve or the like);
    c) applying a forward solution to the first proposed function Funct. 1A to determine a reconstructed second function Funct. 2A corresponding to a set of reconstructed values S2A of the second variable as a function of the independent variable. The forward solution can be one which has been determined to define a good approximation of a relationship between the second variable and the first variable under the conditions used (e.g., Equation 4 in the case of flux and measured concentration);
    d) comparing the reconstructed second function Funct. 2A with the second function Funct.2 including, for a set of data from each of the functions Funct. 2A and Funct.2:
        i) deriving a first vector V1 corresponding to the change in the reconstructed second variable values S2A for a plurality of data sets between independent variable $t_1$ and $t_2$, where independent variable $t_2$ is spaced from $t_1$. For example, $t_1$ may be $[0,1, 2, 3 \ldots n]$ and $t_2$ may be $[1, 2, 3, 4 \ldots n]$;
        ii) deriving a second vector V2 corresponding to the change in the second variable values S2 for a plurality of data sets between independent variable $t_1$ and $t_2$, as described above;
        iii) determining an angle $\theta A$ between the first and second vectors V1, V2, for the set of data, which may include:
            calculating the dot product of the two vectors V1, V2 and then computing the inverse of the cosine of the dot product divided by the product of the absolute values of the two vectors V1, V2 (see Eqn. 7);
        iv) generating a new reconstructed vector V1A corresponding to a change in new reconstructed values S2B between the set of independent variables $t_1$ and $t_2$, for which an angle $\theta B$ between vectors V1A and V2 is less than $\theta A$;
    e. from the new reconstructed vector V1A, deriving a new proposed first function Funct.1B comprising a set of values S1B of the first variable as a function of time; and
    f. optionally, repeating steps b–e a finite number of times.

A suitable algorithm for use with a computer processor in solving the inverse problem is given below in Table 1. The left hand column represents processor operating steps, the right hand column represents operator inputs. Comments on the steps are noted in italics. The algorithm was written using Matlab version 6.1. However, it will be appreciated that it could be written with any other programming language, such as C, C++, or the like.

TABLE 1

| PROCESSOR STEPS | EXEMPLARY OPERATOR STEPS |
|---|---|
| Data Input | |
| Prompt: (Time interval between measurements in seconds) | t = 360; |
| Prompt: (Diffusion coefficient in $cm^2s^{-1}$) | D = 1.5/1000000 |
| Prompt: (Measured concentration in $molcm^{-3}$) | ActConc = 10^−9*[0, 0.1, 0.12, 0.20, 0.26, 0.34, 0.40, 0.44, 0.50, 0.52, 0.54, 0.58, 0.59, 0.60, 0.62, 0.60] |

TABLE 1-continued

| PROCESSOR STEPS | EXEMPLARY OPERATOR STEPS |
| --- | --- |
| Prompt: (The independent variable with respect to which concentration is measured (time in this case))<br>Prompt: (Enter No. of data points in the measured concentration without the first element which is zero).<br>Prompt: Distance in μm | T = [0 6, 12, 18, 24, 30, 36, 42, 48, 54, 60, 66, 72, 78, 84, 90]<br>I = 15<br><br>z = 20*(1/10000); |

Solving The Inverse Problem

Const = sqrt(sum(ActConc.*ActConc));     (Algorithm determines the amplitude of absolute value of the measured concentration, needed for calculation of angle)
Delta = delta(I, t, D, z)
(delta is a function that calculate the delta response when the parameters I, T, z are inputted)
Fl(1:I + 1) = 1
(Assumes the Proposed Flux to be flat)
i = sqrt(I + 1)
FL = Fl
(To save the starting flux, helps to more easily debug the code in case of an error)
Cl = concentration (Fl, Delta, I, t) (Solving the forward problem using the function concentration that calculates the concentration when Fl, Delta, I, t are inputted)
CL = Cl
(To save the starting concentration, again helps with debugging)
Const1 = sqrt(sum(Cl.*Cl))     (Absolute value of the concentration Cl)
Ratio = Const/Const1
Fl = Fl*Ratio
(Ensures that the Flux vector always has an amplitude that correlates with the amplitude of the measured concentration, prevents the vector from growing/shrinking indiscriminately in the course of the iterations)
Err = err_fun(Fl, Delta, I, ActConc, t) (err_fun is the function that calculates the errors in shape)
The following steps assign counters to keep track of the changes in errors, sizes of actual steps made and the sizes of probing steps.
Eo = Err;
E1 = Err
So = (1/10)*(sqrt(sum(Fl.*F1)))
st = (So/i)
(Probing step size)
                                                  N = 0
A(N + 1) = st; E(N + 1) = Err
B(N + 1) = N; M = 0; C(N + 1) = M
P = 0
(actual iteration to estimate the flux begins)
while(((N − M) == 0)&Err >0)
Err_dir = direction_fun(Err, Fl, Delta, I, ActConc, st, Cl, t); (direction_fun calculates that direction in which the stepping should be made, i.e. should the flux elements be increased or decreased)
dE = Err_dir
s = sqrt(sum(dE.*dE))
St = ((−1*dE)./s)*So
Fl = Fl + St
Previous = Err
Err = err_fun(Fl, Delta, I, ActConc, t)
if
(Err >= Previous)
So = So*(0.382)
Fl = Fl − St
Err = err_fun(Fl, Delta, I, ActConc, t)
C(N + 2) = M
else
Cl = concentration(Fl, Delta, I, t);
Const1 = sqrt(sum(Cl.*Cl));
Ratio = Const/Const1;
Fl = Fl*Ratio;
P = Err;
Err = err_fun(Fl, Delta, I, ActConc, t)
So = So*Ratio;
So = (0.382*((Err)/(Eo − Err))*So)
Eo = Err;
M = M + 1
C(N + 2) = M;
End
st = (1/i)*So;

TABLE 1-continued

| PROCESSOR STEPS | EXEMPLARY OPERATOR STEPS |
|---|---|
| ```
N = N + 1
B(N + 1) = N; A(N + 1) = st; E(N + 1) = Err;
End
R = Fl;
(The result, the flux values that corresponds to the measured
concentration)
Cr = concentration(Fl, Delta, I, t);
(The concentration corresponding the obtained flux calculated to
compare with the measured concentration)
function y = delta(I, dt, D, z)
y(1) = 0;
for i = 2:I + 1
y(i) = exp((-z*z)/(4*D*(i - 1)*dt))/sqrt(pi*D*(i - 1)*dt);
end
(Calculating the delta function of diffusion)
function p = concentration(Flux, Delta, I, dt)
for k = 1:I + 1
sum = 0; J = k;
for j = 1:J
sum = sum + Flux(j)*Delta(J - j + 1)*dt;
end
(Solving the forward problem, i.e. calculating (not experimental
values) concentrations given a flux)
p(k) = sum;
end
function Err = err_fun(Fl, Delta, I, ActConc, t)
AssmConc = concentration(Fl, Delta, I, t);
mag1 = sqrt(sum(AssmConc.*AssmConc));
mag2 = sqrt(sum(ActConc.*ActConc));
Err = acos((sum(ActConc.*AssmConc))/(mag1*mag2));
(Calculating the error between two vectors here concentration by
calculating the angel between them)
Function z = direction_fun(Err, Fl, Delta, I, ActConc, st, Cl, dt)
fl = Fl;
ActConc = ActConc;
amp1 = sqrt(sum(ActConc.*ActConc));
phi = Err;
for i = 1:I + 1;
Cr = concentration(fl, Delta, I, dt);
fl(i) = fl(i) + st;
Conc = concentration(fl, Delta, I, dt);
amp2 = sqrt(sum(Conc.*Conc));
z(i) = acos((sum(ActConc.*Conc))/(amp1*amp2)) - phi;
fl(i) = fl(i) - st;
end
(Using the errors in angle calculated above to estimate how
individual flux elements should be changed to minimize this error)
``` | |

One objective of minimization problems in any area of science and engineering often is to reconstruct the changes in a variable with respect to another variable and the solution to such a problem is obtainable from shape information. The preferred approach hence is to minimize the errors in shape.

Applications include the study of flux of ions/molecules in biological preparations from concentration data in agriculture, medical research, and drug development and testing.

Another application is in correcting data of any kind to subtract the characteristics of the instrument used to obtain the data.

Another application is in transport problems in chemistry and physical chemistry, such as electrochemical science and engineering, or small scale production of pharmaceuticals.

Yet another application is in the analysis of signals of virtually any kind such as the qualitative and/or quantitative evaluation of peaks in chromatography techniques or in spectral analytical approaches.

A wide variety of problems, including deconvolution problems, curve fitting problems, pattern recognition problems, parameter identification or estimation problems, general error minimization problems, and image analysis problems are amenable to solution with the techniques disclosed herein.

It should be noted that conventional correlation analysis techniques use the cosine of dot product of vector 1 and vector 2/[abs(vector 1) times abs(vector 2)] instead of the arc cosine, as is used here. One problem of the conventional approach is that cosine becomes progressively insensitive as similarity becomes better, i.e. where it should be the most sensitive it becomes entirely insensitive. This is due to the nature of cosine near zero degree. The shape approach retains uniform sensitivity toward similarity at any degree of similarity including the closest similarities, i.e., when the angle is close to and around zero.

Without limiting the scope of the invention, the following examples demonstrate the effectiveness of the shape optimization technique.

EXAMPLES

Example 1

Ion-selective microelectrodes are used to monitor secretion of $K+$, $Na+$, $H+$, $Ca2+$, and $Cl-$ from confluent epithelial cell monolayers (Cl.16E) in a Ussing chamber. FIG. 2 shows an Ussing chamber set up with four electrodes used for voltage clamp experiments. Electrodes 48 and 52 are platinum current passing electrodes and electrodes 46 and 50 are Ag/AgCl reference electrodes. The monolayer is stimulated by adding 1 mM adenosine triposphate (ATP) and 50 nM phorbol myristate acetate (PMA). A current is passed across the epithelium by using electrodes 48 and 52 such that a potential (transmembrane potential) across electrodes 46 and 50 is zero. An ion selective microelectrode 42 is placed in the apical side, which simultaneously measures the concentration change corresponding to a specific ion. The ion selective electrode is placed at a close distance (in the order of tens of microns) to the cells to obtain data with good temporal resolution. Precise positioning of the ion selective electrode 44 is achieved using electrochemical impedance in situ to monitor distance.

Normal cells as well as cells modeling cystic fibrosis are stimulated with different secretagogues using apical stimulation. The release of ions is monitored with the respective ion selective microelectrodes 44.

The concentration—time recordings are processed to obtain the corresponding fluxes at the cell layer versus time using deconvolution with mathematical shape recognition. The fluxes are then used to reconstruct the short circuit current across the cell layer that was also monitored simultaneously. The results are the first real time data on ionic secretion from epithelial cells with high temporal resolution. This approach can lead to better understanding of mucus granule exocytosis, as well as trans-membrane secretion processes.

Figure 7A:
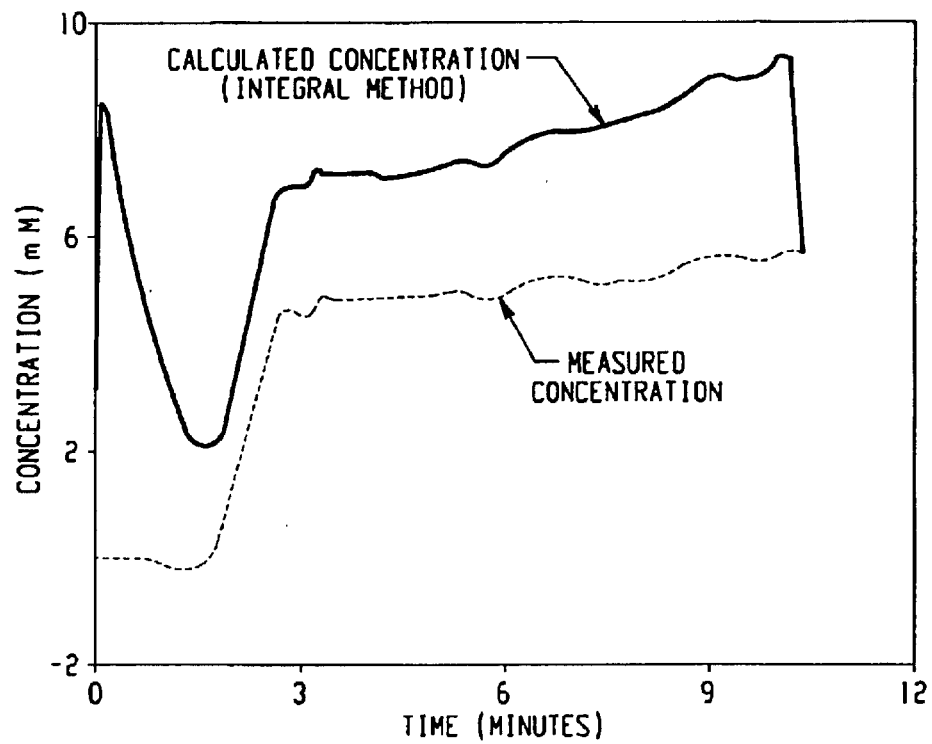
FIG. 7A is a plot of concentration vs. time after apical stimulation with 1 mM ATP and 50 nM PMA for actual (measured) $Cl^-$ concentration (dashed line) and calculated $Cl^-$ concentration (solid line), as determined by deconvolution with a Fourier transform to derive flux values, followed by convolution with an integral method.
Figure 7B:
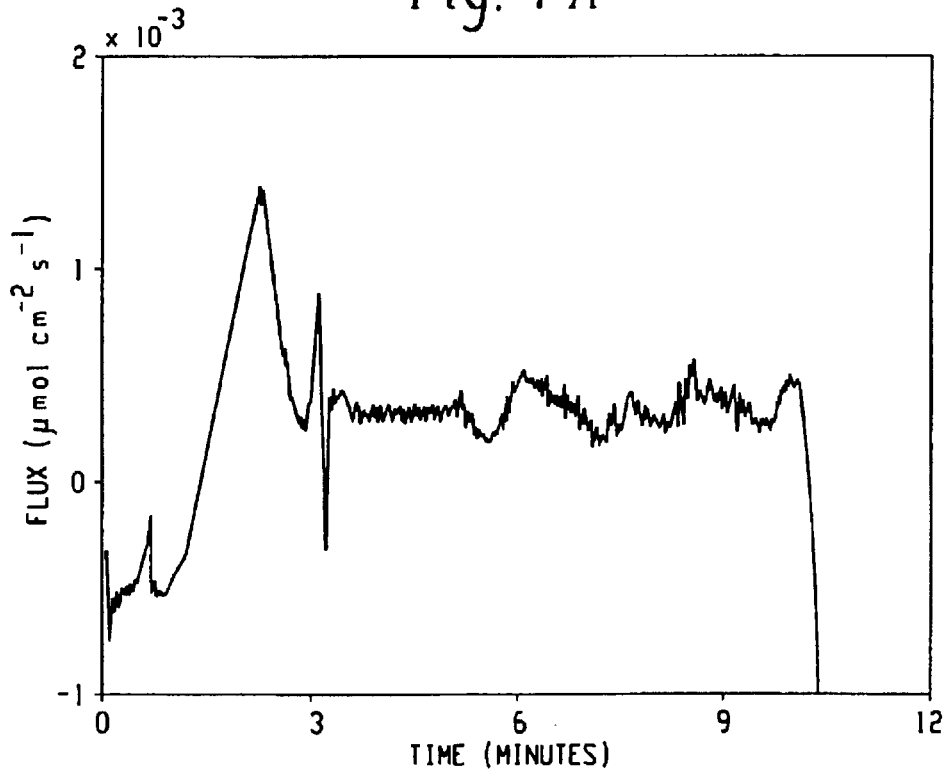
FIG. 7B is a plot of the deconvoluted flux vs. time, derived from the measured concentration plot of FIG. 7A using the Fourier Transform method.

With reference to FIG. 7A, plots of calculated concentration (solid line) and actual (measured) Cl⁻ concentration (dashed line) vs time after apical stimulation with 1 mM ATP and 50 nM PMA are shown. The calculated concentration represents that of a conventional algorithm which applies Fourier transform methods to generate a flux plot and then applies the integral equation (En. 4 above) to generate a calculated concentration plot. The corresponding flux plot is shown in FIG. 7B. It can be seen that the plot is very noisy and can in no way be considered to represent an actual plot of flux. Additionally, the large spike at time t=0 is not realistic, since the flux from a cell is know to exhibit a gradual increase in the initial period. Further, the flux values of below zero are clearly impossible in the system.

Figure 8A:
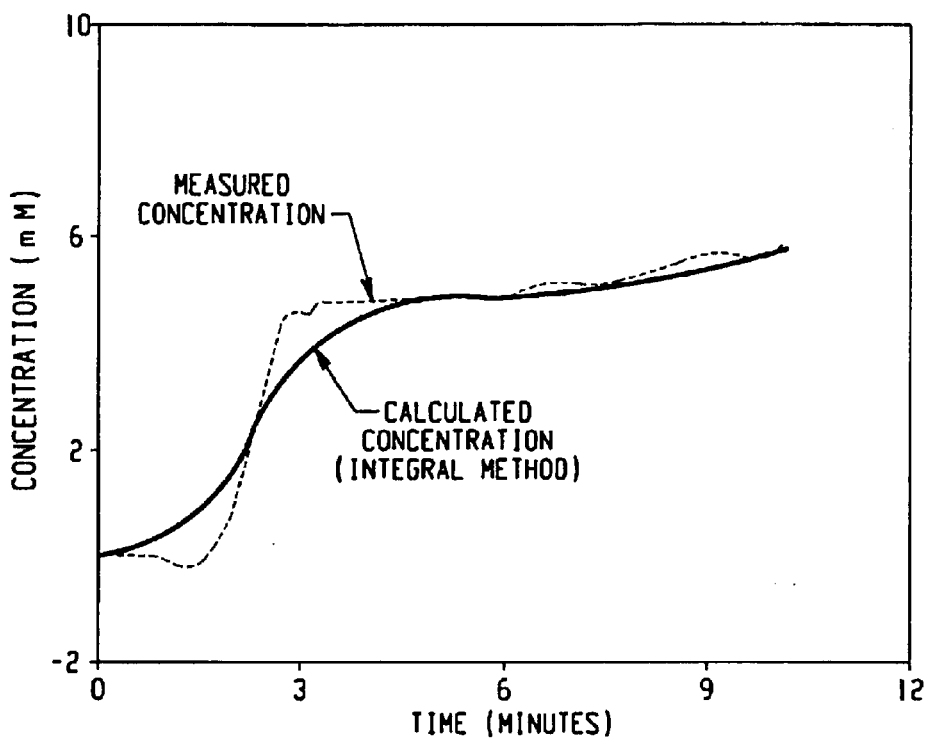
FIG. 8A is a plot of concentration vs. time after apical stimulation with 1 mM ATP and 50 nM PMA for actual (measured) $Cl^-$ concentration (dashed line) and calculated $Cl^-$ concentration (solid line), as determined by deconvolution with a Square Error approach to derive flux values, followed by convolution with the integral method, after six iterations.
Figure 8B:
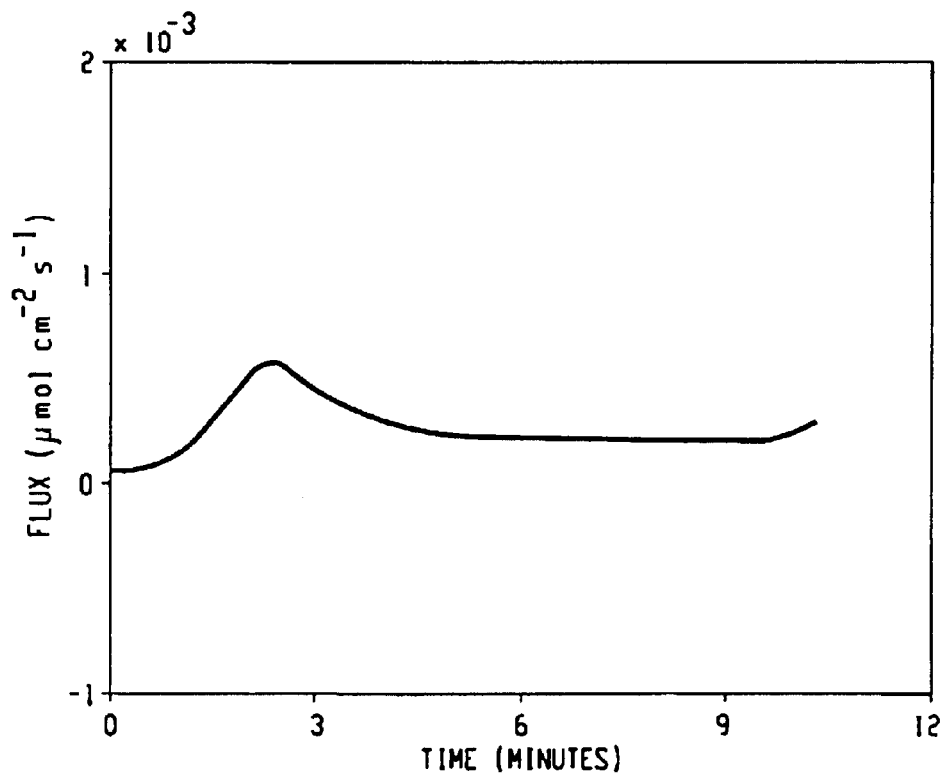
FIG. 8B is a plot of the deconvoluted flux vs. time, derived from the measured concentration plot of FIG. 8A using the Square Error approach method.

With reference now to FIGS. 8A and 8B, similar plots are shown for results generated by a least squares approach, using six iterations. It can be seen that there is a closer fit between the measured and predicted concentration curves, and that the flux curve is closer to an anticipated flux. However, there are still errors in the curve, as exemplified by the positive flux value at time t=0.

Figure 9A:
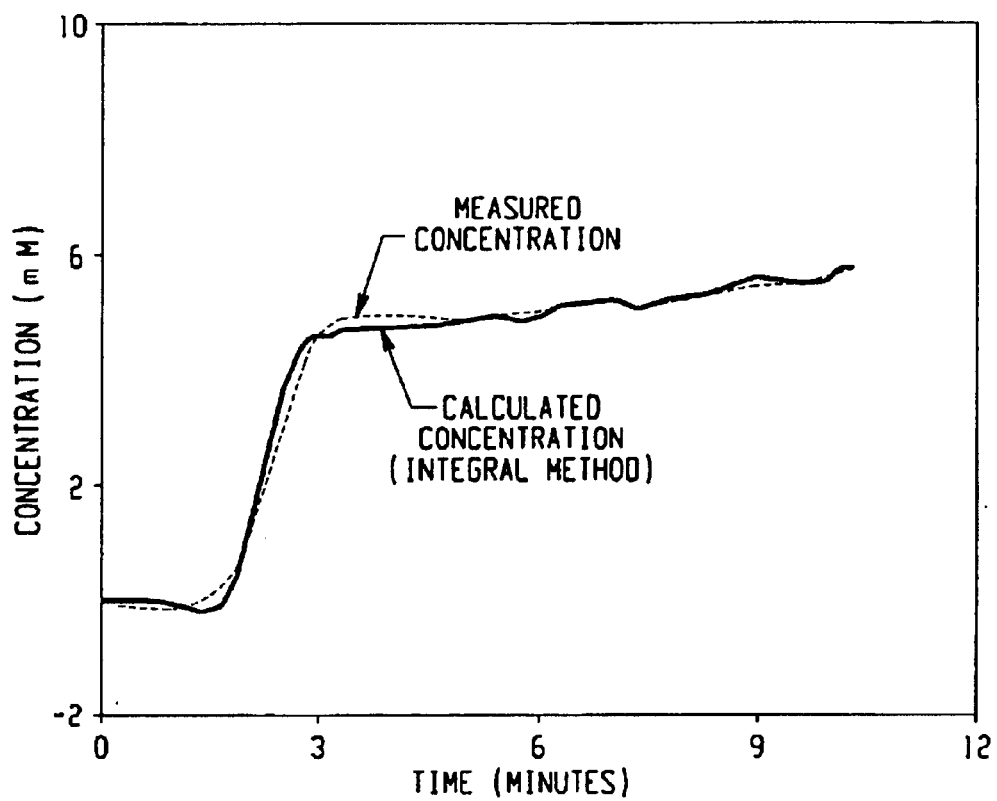
FIG. 9A is a plot of concentration vs. time after apical stimulation with 1 mM ATP and 50 nM PMA for actual (measured) $Cl^-$ concentration (dashed line) and calculated $Cl^-$ concentration (solid line), as determined by deconvolution with a Shape approach to derive flux values, followed by convolution with the integral method, after seven iterations.
Figure 9B:
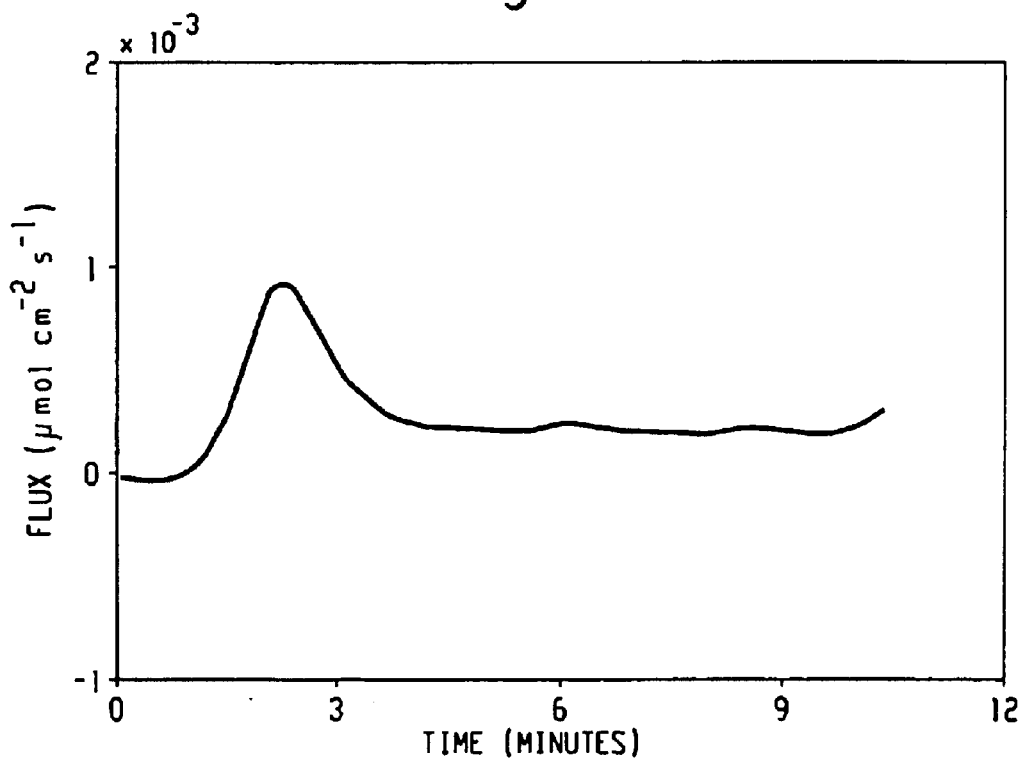
FIG. 9B is a plot of the deconvoluted flux vs. time, derived from the measured concentration plot of FIG. 9A using the Shape approach method.

FIGS. 9A and 9B show similar plots for the shape approach of the present invention, after seven iterations. It can be seen that the measured and reconstructed concentration plots match very closely. The flux plot can thus be expected to represent the actual flux from the cell monolayer over time.

Figure 10A:
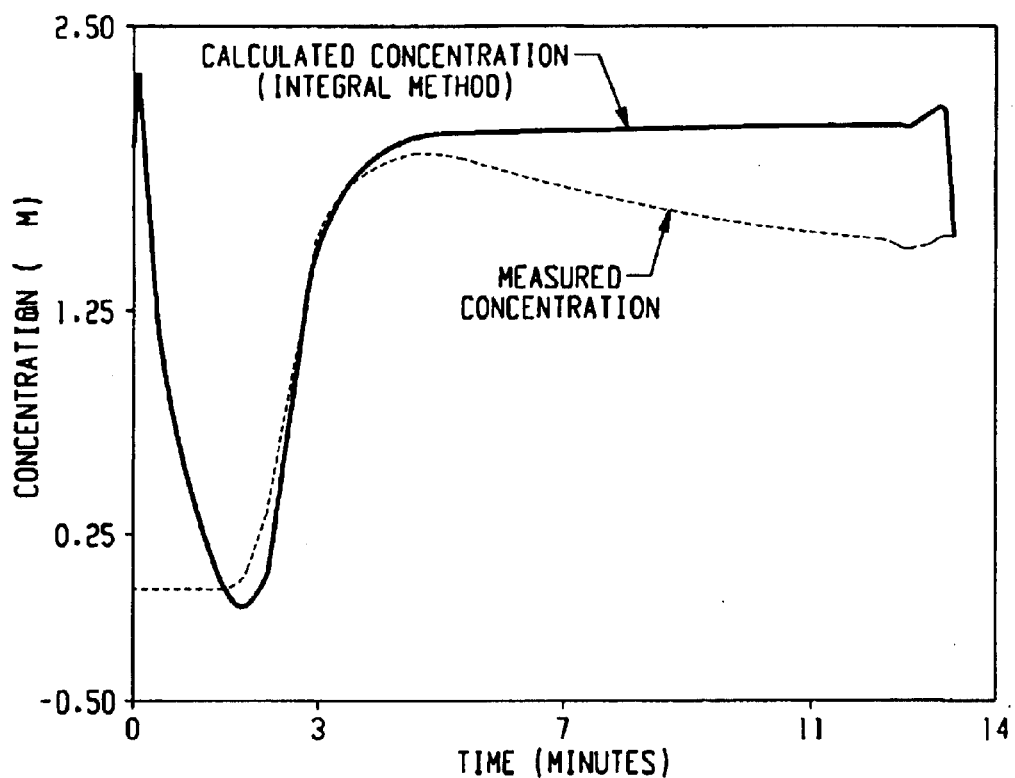
FIG. 10A is a plot of concentration vs. time after apical stimulation with 1 mM ATP and 50 nM PMA for actual (measured) $K^+$ concentration (dashed line) and calculated $K^+$ concentration (solid line), as determined by deconvolution with the Fourier transform method to derive flux values, followed by convolution with the integral method.

FIG. 10A shows plots of calculated concentration (solid line) and actual (measured) K⁺ concentration (dashed line) vs time after apical stimulation with 1 mM ATP and 50 nM PMA. The calculated concentration represents that of a conventional algorithm which applies Fourier transform methods to generate a flux plot and then applies the integral equation (En. 4 above) to generate a calculated concentration plot. The corresponding flux plot is shown in FIG. 10B.

Figure 10B:
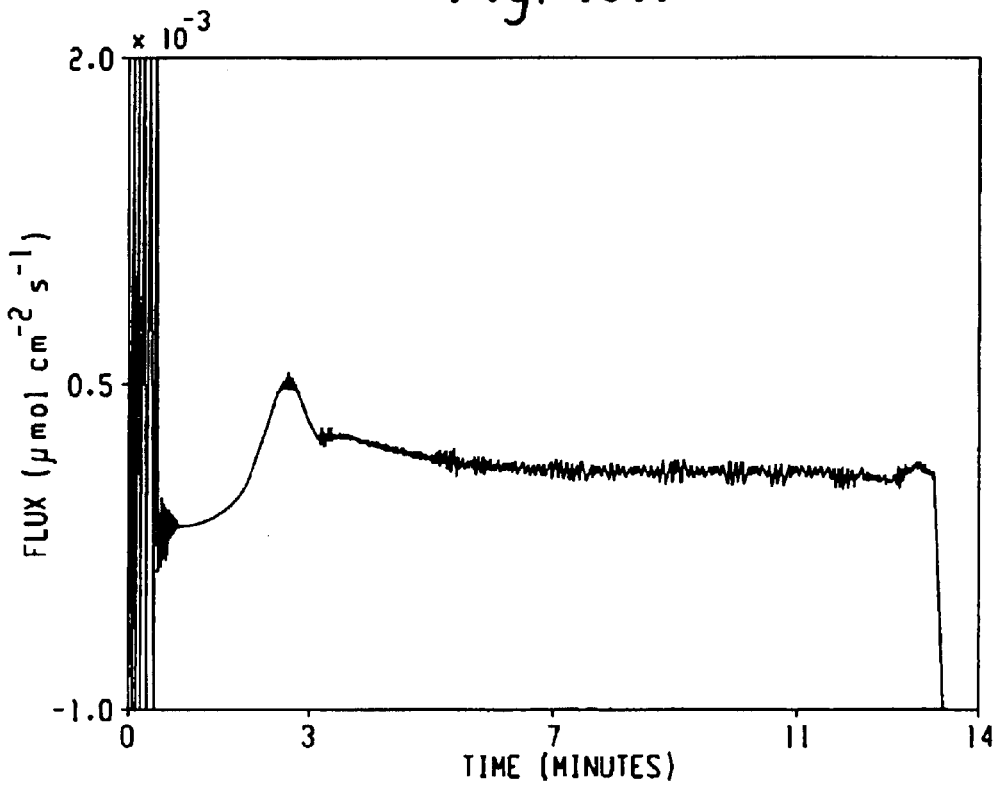
FIG. 10B is a plot of the deconvoluted flux vs. time, derived from the measured concentration plot of FIG. 10A using the Fourier Transform method.
Figure 11A:
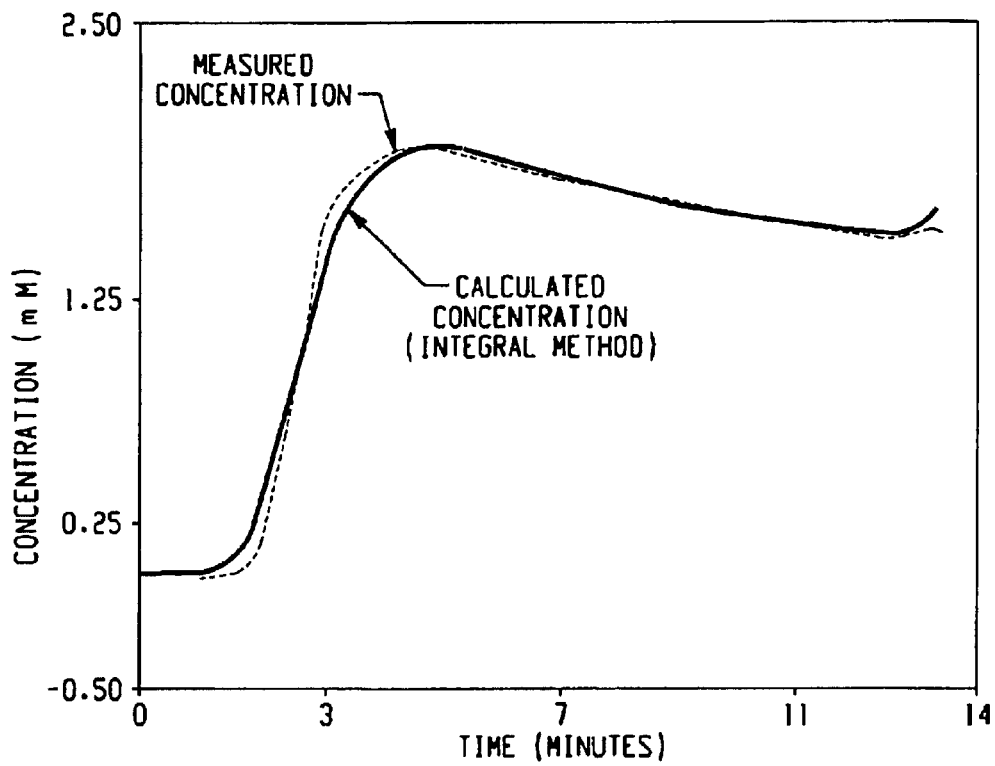
FIG. 11A is a plot of concentration vs. time after apical stimulation with 1 mM ATP and 50 nM PMA for actual (measured) $K^+$ concentration (dashed line) and calculated $K^+$ concentration (solid line), as determined by deconvolution with the Square Error approach to derive flux values, followed by convolution with the integral method, after fourteen iterations.
Figure 11B:
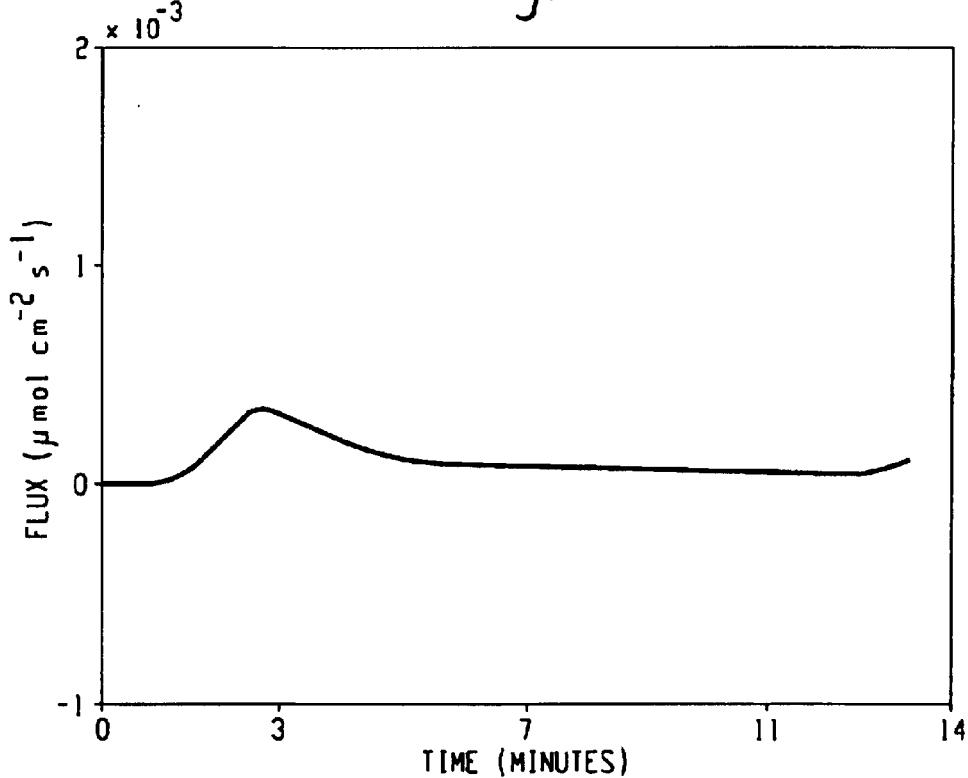
FIG. 11B is a plot of the deconvoluted flux vs. time, derived from the measured concentration plot of FIG. 11A using the Square Error approach method.
Figure 12A:
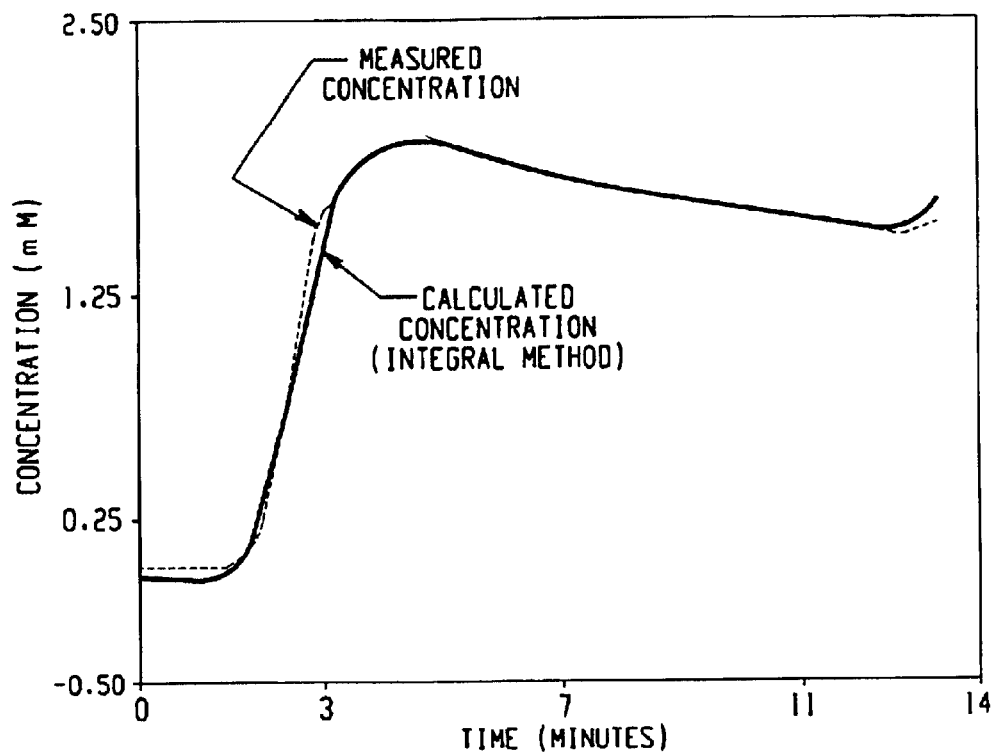
FIG. 12A is a plot of concentration vs. time after apical stimulation with 1 mM ATP and 50 nM PMA for actual (measured) $K^+$ concentration (dashed line) and calculated $K^+$ concentration (solid line), as determined by deconvolution with the Shape approach to derive flux values, followed by convolution with the integral method, after eight iterations.
Figure 12B:
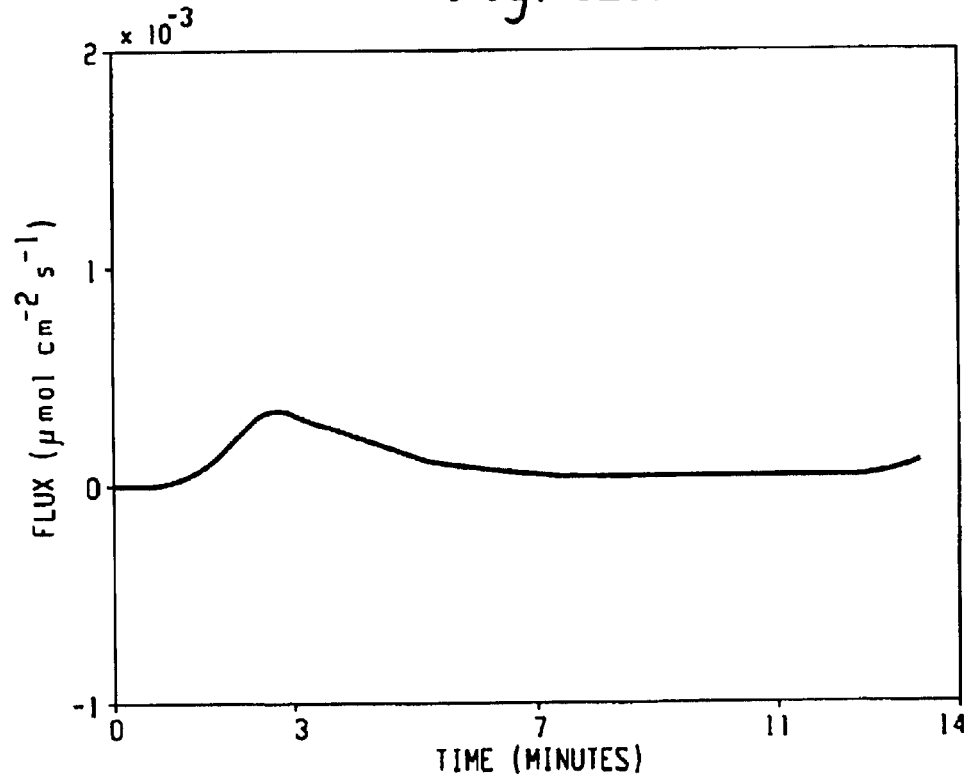
FIG. 12B is a plot of the deconvoluted flux vs. time, derived from the measured concentration plot of FIG. 12A using the Shape approach method.

FIGS. 11A and 11B show similar plots to FIGS. 10A and 10B, for results generated by a least squares approach, using fourteen iterations. FIGS. 12A and 12B show corresponding plots using the shape approach and eight iterations.

Example 2

Reconstruction drug efflux data from drug resistant (CH$^R$C5) and drug sensitive (AUXB1) cancer cell lines is desirable in the context of MDR (Multi Drug Resistance) studies in cancer cell lines. Quantitative understanding of drug efflux patterns can assist in identifying the mechanisms for MDR. Earlier studies were carried out without the benefit of the shape method for calculating efflux, hence certain assumptions were made to ascertain flux patterns during the initial time period of drug efflux measurements (see: Yi, C., Gratzl M. "Continuous in Situ Electrochemical Monitoring of Doxorubicin Efflux from Sensitive and Drug-Resistant Cancer Cells," Biophys. J. 75: 2255–2261(1998)).

In order to estimate flux, it was assumed that the efflux from the cells does not vary significantly during the first three measurement periods of 18 min. For this short period, the medium was assumed to be semi-infinite. Hence the following equation was used to calculate flux.

$$C(t) = 2E\sqrt{\frac{t}{\pi D}}$$

In the above equation E is the constant flux density, and all other variables are as described above. Recent studies with the shape approach have found that this assumption of an initial constant flux is not valid for drug resistant cell lines, because of the difference in efflux mechanisms.

Figure 13A:
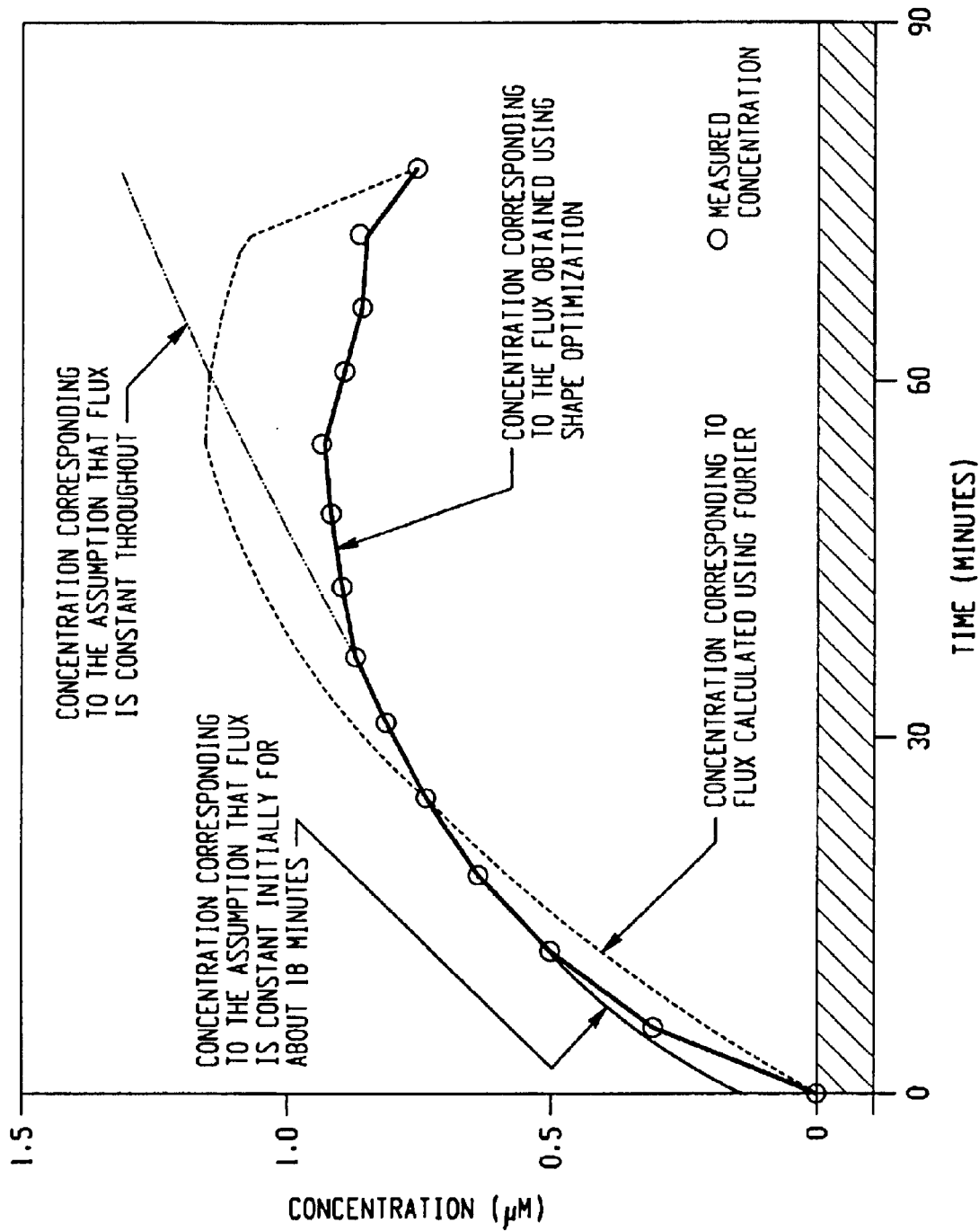
FIG. 13A is a plot of measured concentration and reconstructed concentration vs. time for a drug resistant cell line, respectively, using four methods i) assuming flux to be constant for first eighteen minutes; ii) assuming flux to be constant throughout; iii) backcalculating flux using Fourier transform method; and iv) obtaining the flux using the shape optimization method.
Figure 13B:
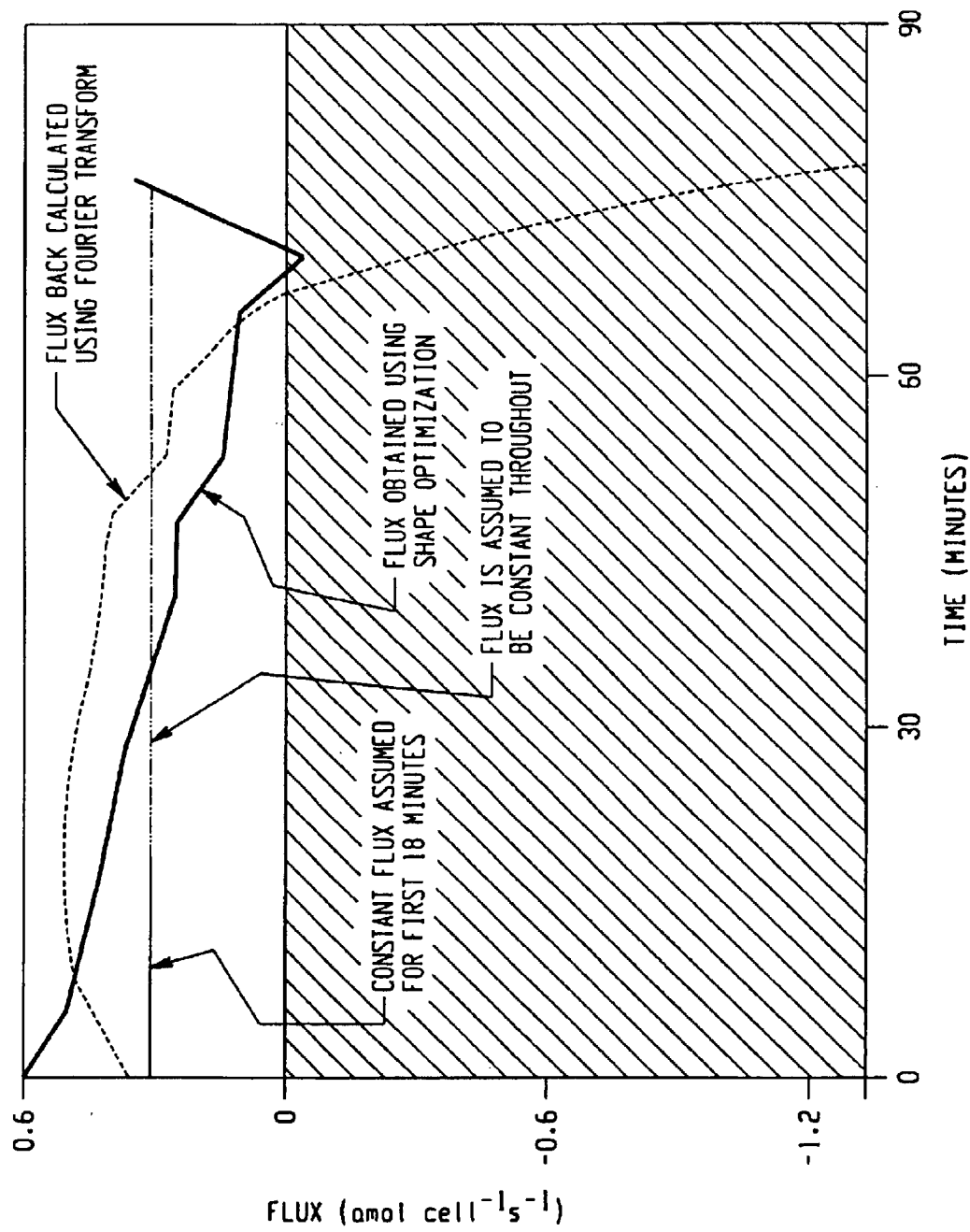
FIG. 13B is a plot of flux vs. time using methods i)–iv) of FIG. 13A, for the drug resistant cell line.

FIGS. 13A and 13B show the concentrations and efflux patterns corresponding to the concentrations for the drug resistant cell line, respectively. It can be seen that the flux back calculated using shape approach fits the measured concentration very well and as expected it clearly indicates that the assumption of a constant flux in the initial time period is not valid. The flux back calculated using Fourier transform has very large negative values as indicated by the shaded regions in the figure and it does fit the measured concentration. This is also true for the case when flux is assumed to be constant throughout.

Figure 13C:
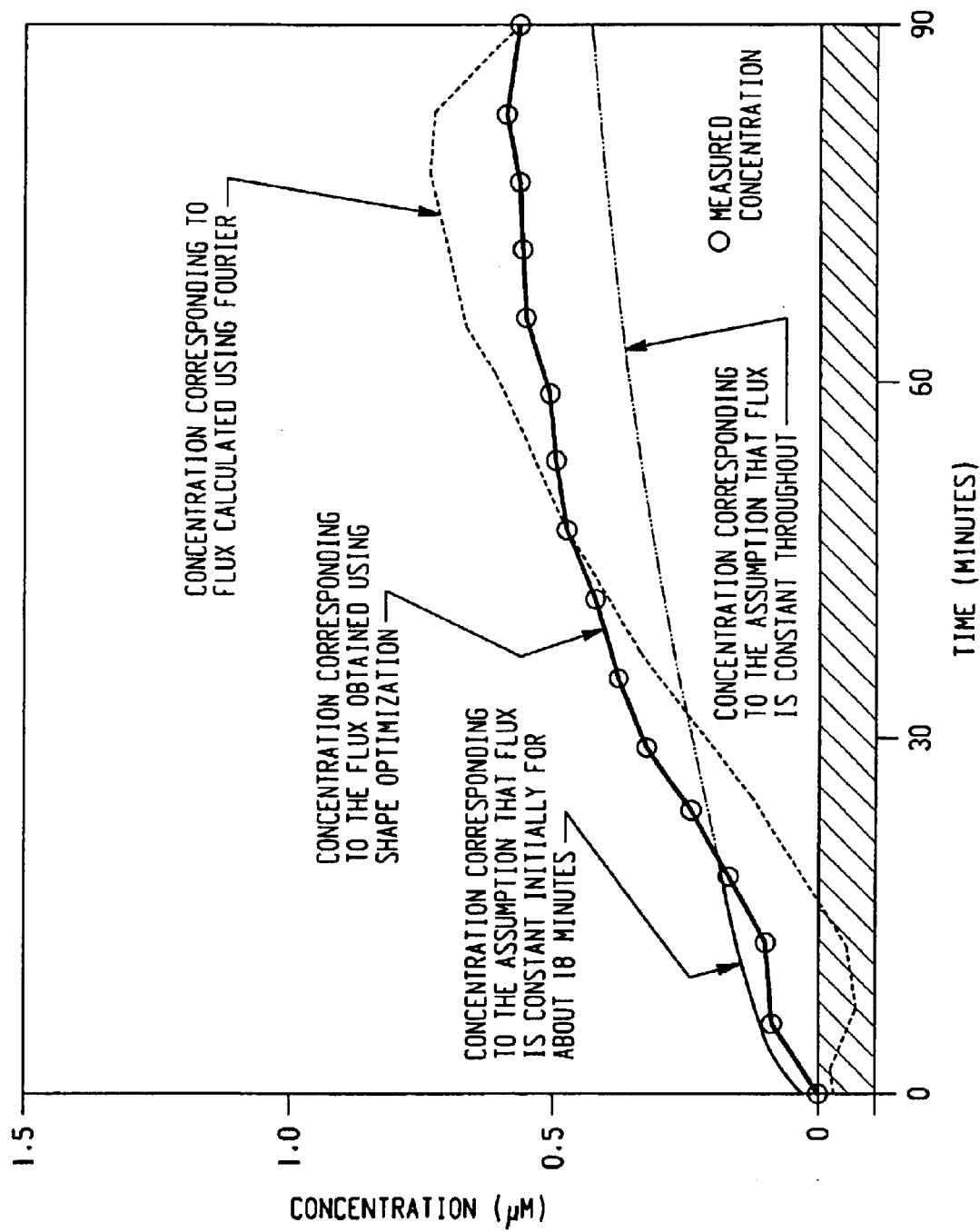
FIG. 13C is a plot of measured concentration and reconstructed concentration vs. time for a drug sensitive cell line, respectively, using the four methods of FIG. 13A.
Figure 13D:
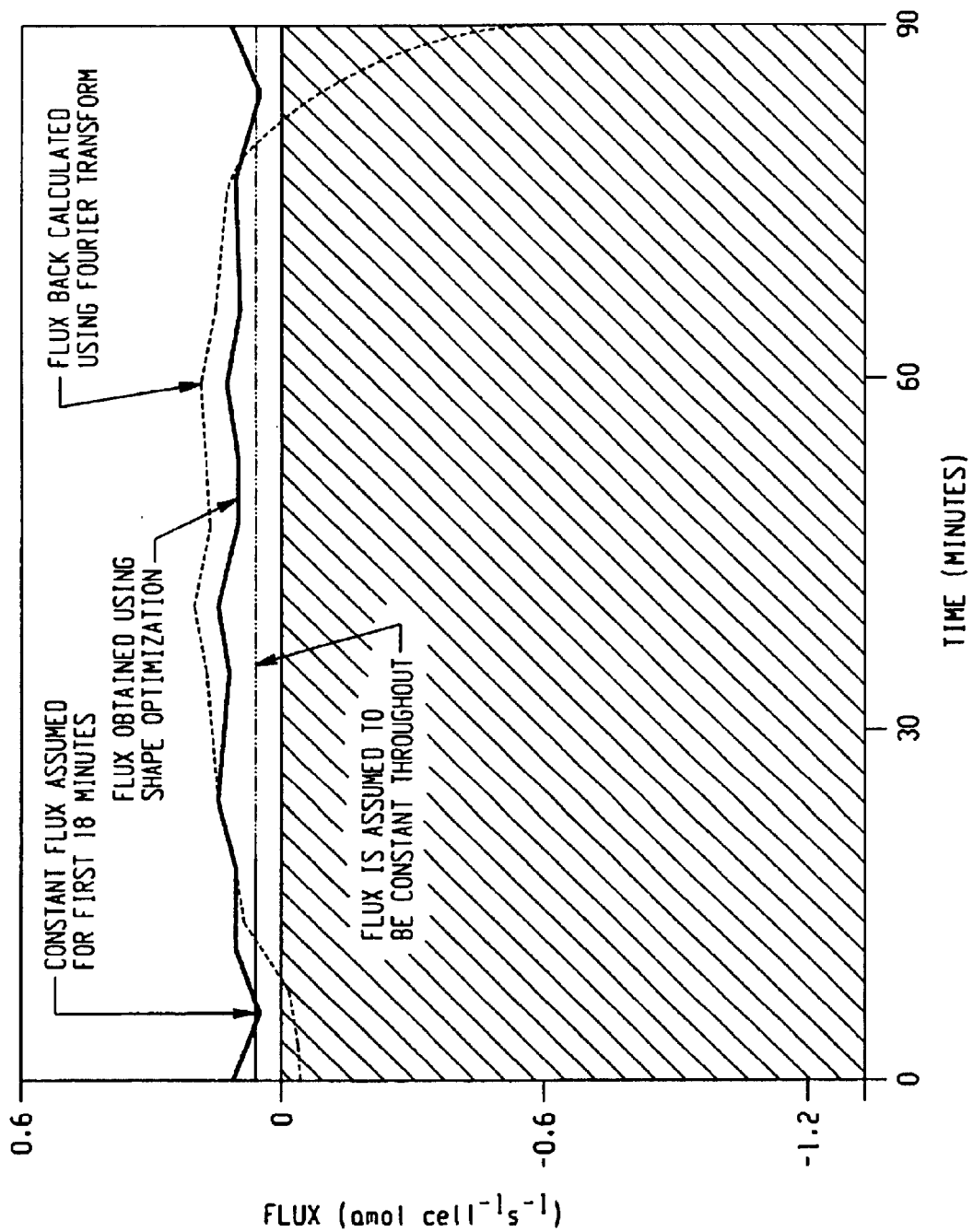
FIG. 13D is a plot of flux vs. time using methods i)–iv) of FIG. 13A, for the drug sensitive cell line.

FIGS. 13C and 13D show the concentrations and efflux patterns corresponding to the concentrations for the drug sensitive cell line, respectively. These figures indicate the flux calculated using shape approach fit the measured concentration very well. Flux calculated using Fourier transform has large negative values as indicated by the shaded regions and does not fit the measured concentration. The assumption that the flux is a constant initially is not so far from reality in the case of drug sensitive cell lines, as shown in the figure.

These results demonstrate that the shape optimization is a powerful and efficient technique to calculated flux information. This approach not only provides the physiologically relevant data but also an insight into physiological processes.

The invention has been described with reference to the preferred embodiment. Obviously, modifications and alterations will occur to others upon reading and understanding the preceding detailed description. It is intended that the invention be construed as including all such modifications and alterations insofar as they come within the scope of the appended claims or the equivalents thereof.

Having thus described the preferred embodiments, the invention is now claimed to be:

1. A computer-implemented method for determining an approximation of a first function (Funct. 1) from a second function (Funct. 2), where there is a forward solution for calculating the second function from the first function, the first function describing the relationship of a first variable to an independent variable, the second function describing the relationship of a second variable to the independent variable, the second variable being one that is ascertainable, comprising:

a) providing the second function (Funct. 2);
b) applying a shape approach method to produce the approximation of the first function (Funct. 1), which characterizes a similarity if two functions by computer-implemented instructions causing a ccomputer to compute an angle between the two functions when they are treated as two vectors in an n dimensional space where n is a number of data points to produce the approximation of the first function (Funct. 1) including:
comparing a shape of the second function (Funct. 2) with a shape of a reconstructed second function (Funct. 2A) derived from a proposed first function (Funct. 1a), the proposed first function describing a proposed relationship of the first variable to the independent variable;
c) optionally, repeating step b a finite number of times.

2. The method of claim 1, wherein step b) includes:
b1) proposing the first proposed function (Funct. 1A);
b2) applying the forward solution to the first proposed function (Funct. 1A) to determine the reconstructed second function (Funct. 2A);
b3) causing a computer to compare the reconstructed second function (Funct. 2A) with the second function (Funct. 2) for a set of data from each of the functions.

3. The method of claim 2, where step b3) includes:
b3i) generating a first vector (V1A) representing, for a plurality of data sets, the change in the reconstructed second function (Funct. 2A) between independent variables $t_1$ and $t_2$, where independent variable $t_2$ is spaced from $t_1$;
b3i) generating a second vector (V2A) representing, for a plurality of data sets, the change in the second function (Funct. 2) between independent variables $t_1$ and $t_2$; and
b3ii) determining an angle (8A) between the first and second vectors (V1A, V2A), for the set of data.

4. The method of claim 3, further including:
proposing a second proposed first function (Funct. 1B), the second proposed first function describing a proposed relationship of the first variable to the independent variable;
applying the forward solution to the second proposed first function (Funct. 1B) to generate a second reconstructed second function (Funct. 2B);
computer instructions causing a computer to generate a third vector (V1B) representing, for a plurality of data sets, the change in a second reconstructed second function (Funct. 2B) between independent variables $t_1$ and $t_2$, in which an angle θB between vectors V1B and V2A is less than θA.

5. The method of claim 1, wherein the first function (Funct. 1) corresponds to a first plurality of values (S1) of the first variable as a function of the independent variable and the second function (Funct. 2) corresponds to second plurality of values (S2) of a second variable as a function of the independent variable.

6. The method of claim 1, wherein the independent variable is time.

7. The method of claim 2, wherein the step of proposing the first proposed function (Funct. 1A) includes proposing the first variable to be constant with respect to the independent variable.

8. The method of claim 2, wherein the step of proposing the first proposed function (Funct. 1A) includes computer instructions causing a computer to access a look up table of previously developed relationships of the first variable with the independent variable.

9. The method of claim 2, wherein the forward solution describes a relationship between the first function and the second function.

10. The method of claim 1, wherein the first variable is flux, the second variable is concentration and the independent variable is time.

11. The method of claim 10, wherein the first and second variables are related by the expression:

$$C_z(t) = \int_0^t F(t')\delta(t-t')dt' \qquad (4)$$

where C is the measured concentration expressed as a function of distance z from the source and time;

F (t') represents the flux at the surface at a time t', corresponding to the time at which the emitted flux corresponding to the measured concentration was generated; and δ represents the effect of secretion at a source over a period of time.

12. The method of claim 2, wherein step b3ii) includes:
calculating the dot product of the two vectors V1A, V2A;
computer instructions causing a computer to compute the inverse of the cosine of the dot product divided by the product of the absolute values of the two vectors V1A, V2A.

13. A computer implemented method for determining an approximation of a flux of a species from a source over time from concentration to the species measured a distance from the source over, comprising:

a) providing a function of the measured concentration over time;
b) proposing a function of the flux over time;
c) applying a forward solution which relates the flux to the concentration to generate a reconstructed function of the concentration over time;
d) comparing the reconstructed function of the concentration with the function of the measured concentration, including:
computer instructions causing a computer to compute an angle between the two functions when they are treated as two vectors in an n dimensional space where n is a number of data points;
e) modifying the proposed function of the flux over time to provide a second proposed function of flux over time, such that when step d is repeated to angle is decreased in value; and
f) optionally, repeating steps d and e) a finite number of times to derive the approximation of the flux.

14. The method of claim 13, wherein the forward solution is:

$$C_z(t) = \int_0^t F(t')\delta(t-t')dt' \quad (4)$$

where C is the measured concentration expressed as a function of distance z from the source and time;

F (t') represents the flux at the surface at a time t', corresponding to the time at which the emitted flux corresponding to the measured concentration was generated; and δ represents the effect of secretion at a source over a period of time.

15. The method of claim 14, wherein δ is derived using the expression:

$$\delta_{z,t} = \frac{1}{\sqrt{\pi D t}} \exp\left(\frac{-z^2}{4Dt}\right) \quad (3)$$

where D is the diffusion constant.

16. The method of claim 13, wherein step f) includes repeating steps di) and diii) and e) about 5–10 times.

17. The method of claim 13, wherein step f) includes repeating steps di) and diii) and e) for fewer number of times than is needed to achieve a value of the angle of zero, to minimize the effects of extraneous errors on the flux.

18. The method of claim 13, further comprising:
using a processor programmed with an algorithm to complete at least one of steps a)–f).

19. The method of claim 13, wherein the proposed function of the flux over time assumes the flux is constant with time.

20. The method of claim 13, wherein the source is a monolayer of cells and the species includes an ion.

21. The method of claim 20, wherein step a) includes:
measuring the concentration of the ion over time in a liquid medium at a distance z from the cell monolayer and generating a plot of the measured concentration vs. time.

22. The method of claim 13, wherein the step determining the angle includes:
calculating the dot product of the two vectors and then computing the inverse of the cosine of the dot product divided by the product of the absolute values of the first and second vectors.

23. The method of claim 22, wherein the step of determining the angle includes applying the equation:

θ=arc cos {dot product of vector 1 and vector 2/[abs(vector 1) times abs(vector 2)]} (7)

where θ is the angle.

24. The method of claim 13, wherein step d includes:
(i) for a plurality of data sets taken from the reconstructed function of the concentration over time, generating a first vector representing, the change in the reconstructed concentration between times $t_1$ and $t_2$, where $t_2$ is spaced from $t_1$;

ii) for a plurality of data sets taken from the function of the concentration over time, generating a second vector representing the change in the concentration between times $t_1$ and $t_2$; and iii) determining an angle between the first and second vectors for the set of data.

* * * * *